(12) United States Patent
Keppler

(10) Patent No.: US 7,057,059 B2
(45) Date of Patent: Jun. 6, 2006

(54) TUMOR-INHIBITING PLATINUM (II) OXALATE COMPLEXES

(75) Inventor: Bernhard Keppler, Hockenheim (DE)

(73) Assignee: Faustus Forschungs CIE. Translational Cancer Research GmbH, Leipzig (DE)

( * ) Notice: Subject to any disclaimer, the term of this patent is extended or adjusted under 35 U.S.C. 154(b) by 0 days.

(21) Appl. No.: 11/011,433

(22) Filed: Dec. 14, 2004

(65) Prior Publication Data

US 2005/0143455 A1 Jun. 30, 2005

Related U.S. Application Data

(63) Continuation of application No. PCT/EP03/06323, filed on Jun. 16, 2003.

(30) Foreign Application Priority Data

Jun. 14, 2002 (DE) ................. 102 26 592

(51) Int. Cl.
*C07F 15/00* (2006.01)
*A61K 31/28* (2006.01)

(52) U.S. Cl. ...................... 556/137; 514/492
(58) Field of Classification Search ................ 556/137; 514/492
See application file for complete search history.

(56) References Cited

U.S. PATENT DOCUMENTS

| 4,291,027 A | 9/1981 | Hoeschel et al. |
| 4,359,425 A | 11/1982 | Totani et al. |
| 4,670,458 A | 6/1987 | Hlavka et al. |
| 4,716,157 A | 12/1987 | Bitha et al. |

FOREIGN PATENT DOCUMENTS

| EP | 0 310 260 A2 | 4/1989 |
| EP | 0 464 210 A1 | 1/1992 |
| EP | 0 646 589 A2 | 4/1995 |
| EP | 0 801 070 A2 | 10/1997 |
| JP | 61-037794 A | 2/1986 |

OTHER PUBLICATIONS

Galanski et al., European Journal of Medicinal Chemistry, vol. 39, No. 8, pp. 707-714 (2004).*

* cited by examiner

*Primary Examiner*—Porfirio Nazario-Gonzalez
(74) *Attorney, Agent, or Firm*—Akin Gump Strauss Hauer & Feld, LLP

(57) ABSTRACT

A tumor-inhibiting platinum (II) oxalate complex and its use as a therapeutic agent are provided, in particular as a tumor-inhibiting medicament. The complex may be compounds of the general formula (I),

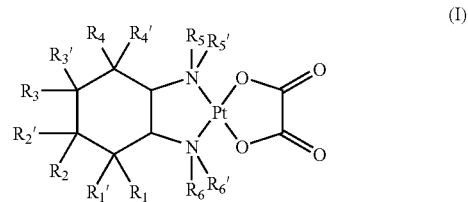

(I)

wherein the substituents $R^1$, $R^{1'}$, $R^2$, $R^{2'}$, $R^3$, $R^{3'}$, $R^4$, and $R^{4'}$ are independently selected from the group consisting of hydrogen, unsubstituted or substituted alkyl, unsubstituted or substituted alkenyl, unsubstituted or substituted cycloalkyl, unsubstituted or substituted cycloalkenyl, unsubstituted or substituted aryl and unsubstituted or substituted alkylaryl radicals, the substituents $R^5$, $R^{5'}$, $R^6$, and $R^{6'}$ are independently selected from the group consisting of hydrogen, unsubstituted or substituted alkyl, and unsubstituted or substituted alkenyl radicals, and wherein optionally in each case at least two of the substituents $R^1$, $R^{1'}$, $R^2$, $R^{2'}$, $R^3$, $R^{3'}$, $R^4$, and $R^{4'}$ can form with one another at least one unsubstituted or substituted alkylene, unsubstituted or substituted alkenylene radical or an unsubstituted or substituted aromatic ring, and wherein optionally at least one of the carbon atoms of the cyclohexane ring bearing the substituents $R^1$, $R^{1'}$, $R^2$, $R^{2'}$, $R^3$, $R^{3'}$, $R^4$, and $R^{4'}$ is replaced by a heteroatom, and if the heteroatom is oxygen, the substituents $R^1$, $R^{1'}$, $R^2$, $R^{2'}$, $R^3$, $R^{3'}$, $R^4$, and $R^{4'}$ can additionally be hydroxy radicals, and pharmaceutically compatible salts of them, provided that at least one of the substituents $R^1$, $R^{1'}$, $R^2$, $R^{2'}$, $R^3$, $R^{3'}$, $R^4$, or $R^{4'}$ is not equal to hydrogen and the substituents $R^1$ or $R^{1'}$ and $R^4$ or $R^{4'}$ do not form any unsubstituted $C_{1-2}$-alkylene radical with one another.

9 Claims, 4 Drawing Sheets

TUMOR-INHIBITING PLATINUM (II) OXALATE COMPLEXES

CROSS-REFERENCE TO RELATED APPLICATIONS

This application is a continuation of International Application No. PCT/EP03/06323, filed Jun. 16, 2003, and the disclosure of which is incorporated herein by reference.

BACKGROUND OF THE INVENTION

The invention relates to tumor-inhibiting platinum (II) oxalate complexes and their use as therapeutic agents, in particular as tumor-inhibiting medicaments.

It is known that some platinum complexes have tumor-inhibiting effects. Apart from cisplatinum, carboplatinum and oxaliplatinum with the following structure

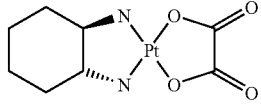

represent the two most important known platinum active substances for combating tumors, wherein in oxaliplatinum the leaving group of the complex with its use as an anti-tumor agent is oxalate. In particular, cisplatinum however has serious side-effects, such as renal toxicity, myelosuppression and ototoxicity.

Therefore, especially oxaliplatinum has, with a bidentate trans-R,R-1,2-diaminocyclohexane ligand and a similarly bidentate oxalato ligand with an effective spectrum deviating from the other two platinum (II) complexes, interesting properties as a cancer therapeutic agent. An advantage with the use of oxaliplatinum as an anti-tumor agent is particularly its lower toxicity in comparison to cisplatinum. However, oxaliplatinum has other undesirable side-effects, such as strong neuropathy.

So far, for the modification of this basic framework and the complex properties the leaving group of the complex was varied. Therefore, in U.S. Pat. No. 4,168,846 cisplatinum (II) complexes with trans-L-1,2-diaminocyclohexane as the ligand without substituents on the cyclohexane ring are described, wherein the complexes, apart from oxalate, have as leaving group malonate and substituted derivatives of malonic acid.

The use of higher dicarboxylic acids or dicarboxylic acid derivatives as ligands in platinum (II) complexes, such as malonate or succinate, is, for example, also described in JP 61-037794.

Furthermore, a range of platinum (II) complexes with monodentate anions, such as pyrophosphate, is described in U.S. Pat. No. 4,234,500.

Also, platinum (II) complexes are known which have a modified diaminocyclohexane ligand. For example, in U.S. Pat. No. 4,359,425 platinum (II) complexes are described, which have a special diaminocyclohexane ligand, which is bicyclical and is bridged on the two carbon atoms adjacent to the amino groups by a $(CH_2)_n$ bridge where n=1 or 2. In U.S. Pat. No. 4,670,458 dihydroxylised diaminocyclohexane derivatives are disclosed as diaminocyclohexane ligands.

In addition, substituted cyclohexane derivatives, which have pyrophosphate as the leaving group, are described in U.S. Pat. No. 4,291,027.

BRIEF SUMMARY OF THE INVENTION

An object of this invention is to provide further tumor-inhibiting platinum (II) oxalate complexes. The object is solved by compounds of the general formula (I),

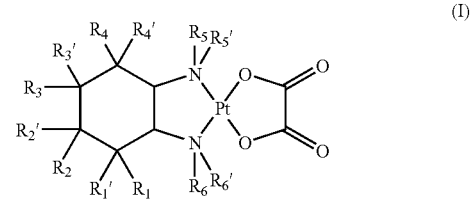

(I)

wherein the substituents $R^1$, $R^{1'}$, $R^2$, $R^{2'}$, $R^3$, $R^{3'}$, $R^4$, and $R^{4'}$ are independently selected from the group consisting of hydrogen, unsubstituted or substituted branched or unbranched alkyl, unsubstituted or substituted branched or unbranched alkenyl, unsubstituted or substituted cycloalkyl, unsubstituted or substituted cycloalkenyl, unsubstituted or substituted aryl and unsubstituted or substituted alkylaryl radicals, the substituents $R^5$, $R^{5'}$, $R^6$, and $R^{6'}$ are independently selected from the group consisting of hydrogen, unsubstituted or substituted branched or unbranched alkyl, and unsubstituted or substituted branched or unbranched alkenyl radicals, wherein optionally in each case at least two of the substituents $R^1$, $R^{1'}$, $R^2$, $R^{2'}$, $R^3$, $R^{3'}$, $R^4$, and $R^{4'}$ can form with one another at least one unsubstituted or substituted alkylene, unsubstituted or substituted alkenylene radical or an unsubstituted or substituted aromatic ring, and wherein optionally at least one of the carbon atoms of the cyclohexane ring bearing the substituents $R^1$, $R^{1'}$, $R^2$, $R^{2'}$, $R^3$, $R^{3'}$, $R^4$, and $R^{4'}$ is replaced by a heteroatom, and if the heteroatom is oxygen, the substituents $R^1$, $R^{1'}$, $R^2$, $R^{2'}$, $R^3$, $R^{3'}$, $R^4$, and/or $R^{4'}$ can additionally be hydroxy radicals, and pharmaceutically compatible salts thereof, provided that at least one of the substituents $R^1$, $R^{1'}$, $R^2$, $R^{2'}$, $R^3$, $R^{3'}$, $R^4$, or $R^{4'}$ is not equal to hydrogen and the radicals $R^1$ or $R^{1'}$ and $R^4$ or $R^{4'}$ do not form any unsubstituted $C_{1-2}$-alkylene radicals with one another.

The substituents $R^1$, $R^{1'}$, $R^2$, $R^{2'}$, $R^3$, $R^{3'}$, $R^4$, $R^{4'}$, $R^5$, $R^{5'}$, $R^6$, and/or $R^{6'}$ can be substituted by halogens, in particular Cl, F or Br, hydroxy, amino, nitro, CN, $CF_3$, $C_1$–$C_4$-alkyl, in particular $C_1$–$C_3$-alkyl, $C_1$–$C_4$-alkoxy, in particular $C_1$–$C_3$-alkoxy, $C_1$–$C_4$-alkylthio, $C_3$–$C_7$-cycloalkyl, in particular $C_3$–$C_6$-cycloalkyl, $C_3$–$C_6$-cycloalkoxy, $C_2$–$C_4$-alkenyl, $C_2$–$C_4$-alkinyl, aryl, heteroaryl, $NR_7R_8$, $COOR_7$, $CONR_7R_8$, $NR_7COR_8$, $NR_7COOR_8$, $S(O)R_7$, $SO_2R_7$, $SO_2NR_7R_8$, $SO_3H$, wherein $R^7$ and $R^8$ signify independently H, $C_1$–$C_4$-alkyl, aryl or heteroaryl or can form a $C_3$–$C_7$-cycloalkyl ring or $C_3$–$C_7$-cycloalkenyl ring.

Preferably, the substituents $R^1$, $R^{1'}$, $R^2$, $R^{2'}$, $R^3$, $R^{3'}$, $R^4$, and $R^{4'}$ are selected independently from the group consisting of hydrogen, $C_1$–$C_{15}$-alkyl, $C_2$–$C_{15}$-alkenyl, $C_3$–$C_{15}$-cycloalkyl, $C_3$–$C_{15}$-cycloalkenyl, $C_6$–$C_{14}$-aryl and $C_1$–$C_{15}$-alkyl-$C_6$–$C_{14}$-aryl radicals.

Particularly preferably the substituents $R^1$, $R^{1'}$, $R^2$, $R^{2'}$, $R^3$, $R^{3'}$, $R^4$, and $R^{4'}$ are selected independently from the group consisting of hydrogen, $C_1$–$C_{10}$-alkyl, $C_2$–$C_{10}$-alkenyl, $C_3$–$C_{10}$-cycloalkyl, $C_3$–$C_{10}$-cycloalkenyl, $C_6$–$C_{10}$-aryl and $C_1$–$C_{10}$-alkyl-$C_6$–$C_{10}$-aryl radicals; in particular the substituents $R^1$, $R^{1'}$, $R^2$, $R^{2'}$, $R^3$, $R^{3'}$, $R^4$, and $R^{4'}$ are selected from the group consisting of hydrogen, $C_1$–$C_6$-alkyl, $C_2$–$C_6$-alkenyl, $C_3$–$C_6$-cycloalkyl, $C_3$–$C_6$-cycloalkenyl, $C_6$–$C_{10}$-aryl and $C_1$–$C_6$-alkyl-$C_6$–$C_{10}$-aryl radicals.

Particularly preferably the substituents $R^1$, $R^{1'}$, $R^2$, $R^{2'}$, $R^3$, $R^{3'}$, $R^4$, $R^{4'}$ are selected from the group consisting of hydrogen, $C_1$–$C_{10}$-alkyl radicals, in particular methyl, ethyl, n-propyl, i-propyl, n-butyl, branched butyl radicals, n-pentyl, branched pentyl radicals, n-hexyl and branched hexyl radicals, $C_3$–$C_{10}$-cycloalkyl radicals, in particular cyclopropyl, cyclobutyl, cyclopentyl and cyclohexyl radicals and $C_6$–$C_{14}$-aryl radicals, in particular phenyl radicals.

The two substituents located on the same carbon atom $R^1$, $R^{1'}$, $R^2$, $R^{2'}$, $R^3$, $R^{3'}$, or $R^4$, $R^{4'}$ can be the same or different.

Preferably one to three, more preferably one or two and especially preferably one of the substituents $R^1$, $R^{1'}$, $R^2$, $R^{2'}$, $R^3$, $R^{3'}$, $R^4$, and $R^{4'}$ are selected from the group consisting of unsubstituted or substituted alkyl, unsubstituted or substituted alkenyl, unsubstituted or substituted cycloalkyl, unsubstituted or substituted cycloalkenyl, unsubstituted or substituted aryl and unsubstituted or substituted alkylaryl radicals and the remaining radicals are hydrogen atoms. The radicals are preferably as described above.

In a particularly preferred embodiment the substituents $R^1$, $R^{1'}$, $R^3$, $R^{3'}$, $R^4$, and $R^{4'}$ are hydrogen and $R^2$ and $R^{2'}$ are selected from the group consisting of hydrogen, $C_1$–$C_6$-alkyl, $C_2$–$C_6$-alkenyl, $C_3$–$C_6$-cycloalkyl, $C_3$–$C_6$-cycloalkenyl and $C_6$–$C_{10}$-aryl radicals and provided that $R^2$ and $R^{2'}$ are not at the same time hydrogen.

Especially preferably, compounds are preferred wherein the substituents $R^1$, $R^{1'}$, $R^3$, $R^{3'}$, $R^4$, and $R^{4'}$ are equal to hydrogen and the substituents $R^2$ or $R^{2'}$ are a $C_1$–$C_6$-alkyl radical, in particular methyl, ethyl, propyl or t-butyl radical or a $C_6$–$C_{10}$-aryl radical, in particular phenyl radical, wherein optionally the other radical $R^2$ or $R^{2'}$ in each case is hydrogen.

Similarly especially preferably, compounds are preferred wherein the substituents $R^1$, $R^{1'}$, $R^3$, $R^{3'}$, $R^4$, and $R^{4'}$ are equal to hydrogen and $R^2$ or $R^3$ is a $C_1$–$C_6$-alkyl radical, in particular methyl, ethyl, propyl or t-butyl radical or a $C_6$–$C_{10}$-aryl radical, in particular phenyl radical, wherein either $R^2$ or $R^{2'}$ is hydrogen.

In a further especially preferred embodiment the substituents $R^1$, $R^{1'}$, $R^4$, and $R^{4'}$ are equal to hydrogen, and $R^2$, $R^{2'}$, $R^3$ and $R^{3'}$ are selected from the group consisting of hydrogen, $C_1$–$C_6$-alkyl and $C_2$–$C_6$-alkenyl radicals, and provided that $R^2$, $R^{2'}$, $R^3$ and $R^{3'}$ are not at the same time hydrogen.

Especially preferably, compounds are preferred wherein the substituents $R^1$, $R^{1'}$, $R^4$, and $R^{4'}$ are equal to hydrogen and the substituents $R^2$, $R_2$, $R^3$ and $R^{3'}$ are a $C_1$–$C_6$-alkyl radical, in particular methyl, ethyl, propyl or t-butyl radical, wherein optionally in each case the other radical $R^2$ or $R^{2'}$, resp. $R^3$ or $R^{3'}$ is hydrogen.

Similarly especially preferably, compounds are preferred wherein the substituents $R^1$, $R^{1'}$, $R^4$, and $R^{4'}$ are equal to hydrogen, $R^2$ or $R^{2'}$ and $R^3$ or $R^{3'}$ are a $C_1$–$C_6$-alkyl radical, in particular a methyl, ethyl, propyl or t-butyl radical, wherein $R^2$ or $R^{2'}$ and $R^3$ or $R^{3'}$ are hydrogen.

When at least two of the substituents $R^1$, $R^{1'}$, $R^2$, $R^{2'}$, $R^3$, $R^{3'}$, $R^4$, and $R^{4'}$ form with one another at least an unsubstituted or substituted alkylene, unsubstituted or substituted alkenylene radical or an unsubstituted or substituted aryl radical, then those that form them are preferably $C_1$–$C_{15}$-alkylene radicals, $C_2$–$C_{15}$-alkenylene radicals or $C_6$–$C_{14}$-aryl radicals. Consequently, bi-, tri- or multi-cyclical radicals are obtained.

It is particularly preferable that in each case two radicals located on adjacent carbon atoms of the cyclohexane ring form with one another one of the previously described radicals. Furthermore, it is especially preferable that a $C_6$–$C_{14}$-aryl radical, in particular a phenyl radical, is annelated via the carbon atoms of the cyclohexane ring bearing the substituents $R^2$, $R^{2'}$ and $R^3$, $R^{3'}$ to the cyclohexane ring.

Also, two radicals located on the same carbon atom of the cyclohexane ring can form together one of the previously described radicals, whereby the respective spiro-compounds are obtained. Especially preferably only two of the radicals together form respectively one of the previously described radicals, whereby a bicyclical system is obtained.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
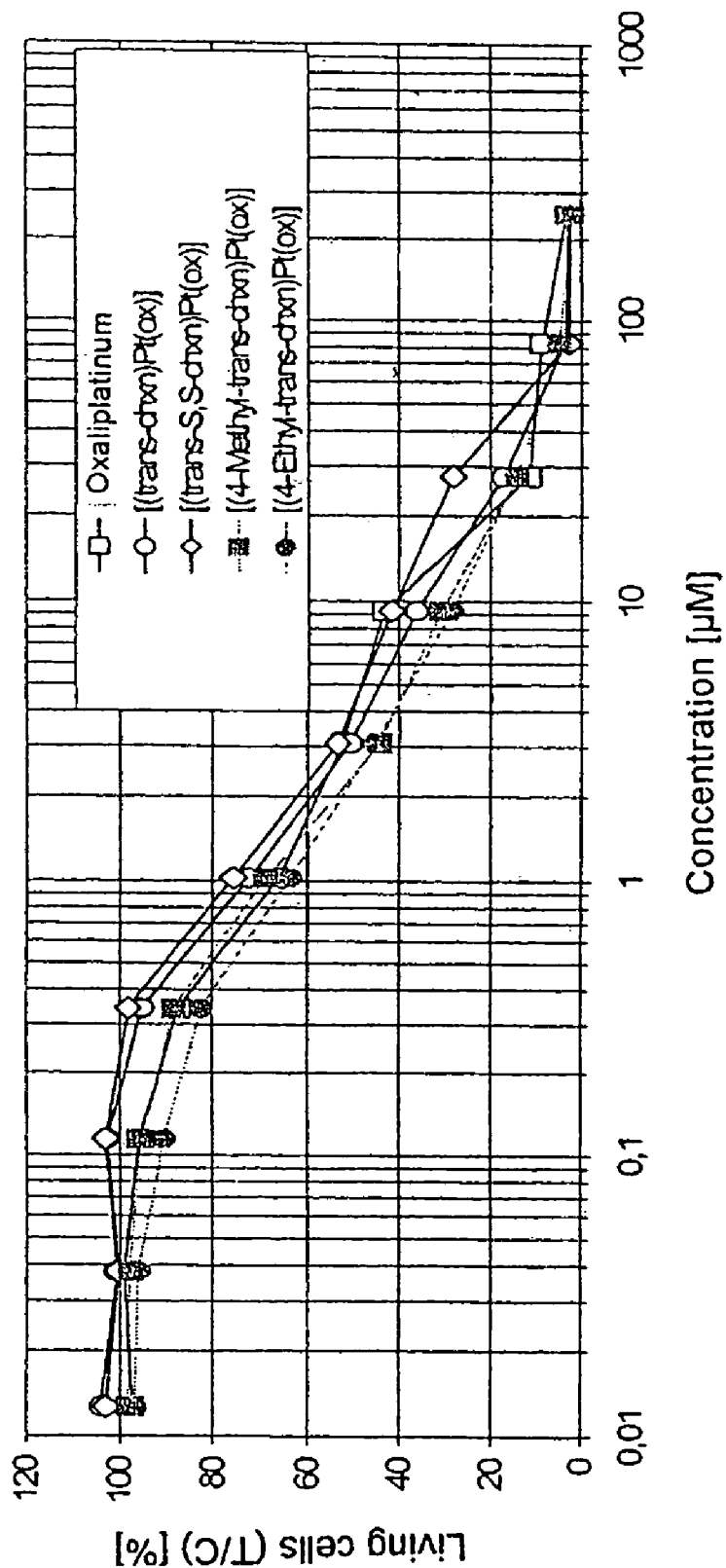
FIG. 1 is a graphical representation of the cytotoxicity test results of the compounds of Examples 1 and 2 plotting the 41M cell line of living cells (T/C) [%] against concentration [μM]

In a preferred embodiment the substituents $R^5$, $R^{5'}$, $R^6$, and $R^{6'}$ are selected independently from the group consisting of hydrogen, $C_1$–$C_6$-alkyl or $C_2$–$C_6$-alkenyl radicals. The $C_1$–$C_6$-alkyl radicals are preferably methyl, ethyl, n-propyl or i-propyl radicals. The $C_2$–$C_6$-alkenyl radicals are preferably ethenyl or propenyl radicals. Furthermore, the substituents $R^5$, $R^{5'}$, $R^6$, and $R^{6'}$ are preferably hydrogen. Preferably $R^5$, $R^{5'}$, $R^6$, and $R^{6'}$ are unsubstituted.

If at least one of the carbon atoms of the cyclohexane ring bearing the substituents $R^1$, $R^{1'}$, $R^2$, $R^{2'}$, $R^3$, $R^{3'}$, $R^4$, and $R^{4'}$ is replaced by a heteroatom, the heteroatom is preferably selected from the group consisting of oxygen, nitrogen and sulphur and it is preferable that one to three, in particular one or two, especially one heteroatom is present.

If one of the carbon atoms of the cyclohexane ring is substituted by a heteroatom, then depending on the binding of the heteroatom, less than two substituents can be bound to the heteroatom. Oxygen and sulphur are, for example, unsubstituted and nitrogen is simply substituted appropriate to the position in the heterocycle by one of the substituents $R^1$, $R^{1'}$, $R^2$, $R^{2'}$, $R^3$, $R^{3'}$, $R^4$, or $R^{4'}$.

Preferably for the heteroatom, oxygen is involved which has been incorporated in place of the carbon atom in the cyclohexane ring bearing the $R^3$ and $R^{3'}$ or $R^2$ and $R^{2'}$, wherein at least one remaining substituent $R^1$, $R^{1'}$, $R^2$, $R^{2'}$, $R^3$, $R^{3'}$, $R^4$, or $R^{4'}$ is not equal to hydrogen.

If the heteroatom is oxygen, the appropriately modified cyclohexane ring can be an amino sugar, e.g. based on glucose.

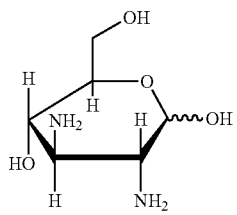

The two amino groups on the cyclohexane ring in the compounds according to the invention can have a cis- or trans-arrangement relative to one another. Preferably they have a trans arrangement. The two carbon atoms of the cyclohexane ring, which bear the amino groups, can have an R,R, S,S, R,S or S,R configuration.

A possible arrangement of the two amino groups and of the heteroatom, oxygen, is illustrated in the following:

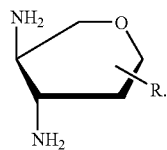

Furthermore, compounds are preferred with which the substituents $R^5$, $R^{5'}$, $R^6$, and $R^{6'}$ are hydrogen and optionally at least one of the carbon atoms of the cyclohexane ring bearing the substituents $R^1$, $R^{1'}$, $R^2$, $R^{2'}$, $R^3$, $R^{3'}$, $R^4$, and $R^{4'}$ is replaced by a heteroatom, and
  if the heteroatom is oxygen, the substituents $R^1$, $R^{1'}$, $R^2$, $R^{2'}$, $R^3$, $R^{3'}$, $R^4$, and $R^{4'}$ are selected independently from the group consisting of hydrogen, unsubstituted or substituted alkyl, unsubstituted or substituted alkenyl, unsubstituted or substituted cycloalkyl, unsubstituted or substituted cycloalkenyl, unsubstituted or substituted aryl and unsubstituted or substituted alkylaryl radicals.

In the sense of this description the terms "alkyl" or "alkenyl" always comprise unbranched or branched "alkyl" or "alkenyl".

The physiologically compatible salts of the compounds according to the invention are preferably selected from the group consisting of organic or inorganic addition salts, which in particular can be formed with the following described anions and cations.

The anions are preferably selected from the group consisting of halogens, such as chloride and bromide, pseudohalogens, phosphate, carbonate, nitrate, perchlorate, sulphate, citrate, lactate, tartrate, maleate, fumarate, mandelate, benzoate, ascorbate, cinnamate, glycollate, methane sulphonate, formiate, malonate, naphthalin-2-sulphonate, salicylate and acetate.

The cations are preferably selected from the group consisting of H+, sodium and potassium cations.

The compounds according to the invention have a surprisingly good tumor-inhibiting effect.

The synthesis of the compounds according to the invention occurs according to known methods, for example, starting from $K_2[PtCl_4]$, whereby the two bidentate ligands are introduced successively. To achieve this, first the tetrachloroplatinate (II) can be reacted with the suitably substituted diamine. The diamine (dichloro)platinum (II) complex can then be activated by reaction with silver nitrate or silver sulphate. The diaqua(diamine) or aqua(sulphato)diamine compound thus obtained can then be transformed into the corresponding compound according to the invention by ligand interchange with oxalic acid or sodium oxalate. For example, (SP-4-3)-(trans-cyclohexane-1,2-diamine-4-methyl)-oxalate platinum (II) can be made as described above.

The following schemes show, using the example of the 4-methyl substituted derivative, possible synthesis paths for the production of the compounds according to the invention.

For the production of (SP-4-3)-(trans-cyclohexane-1,2-diamine-4-methyl)-oxalate platinum (II), isomer mixtures of trans-4-methylcyclohexane-1,2-diamines can be made starting from 4-methylcyclohexanone according to Diagram 1. As can be seen in Diagram 1, after bromification and reaction with hydroxylamine, the dioxime obtained is reduced with sodium in absolute ethanol.

Diagram 1

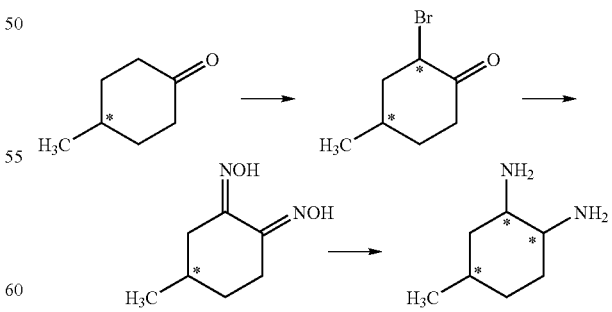

For the production of the other compounds according to the invention the cyclohexanone in Diagram 1 can also be substituted by the substituents $R^1$, $R^{1'}$, $R^2$, $R^{2'}$, $R^3$, $R^{3'}$, $R^4$, and/or $R^{4'}$, as described above. In particular the corresponding derivative can also be made analogously with an ethyl radical instead of a methyl radical. Alternatively, a suitably substituted cyclohexane-1,2-dion derivative, which can be transformed into the corresponding oxime directly as previously described by reaction with hydroxylamine, can be used instead of the substituted cyclohexanone.

Here, isomer mixtures of substituted trans-cyclohexane-1,2-diamine are obtained.

The substituted cyclohexane or cyclohexane-1,2-dion can also be substituted by the substituents $R^1$, $R^{1'}$, $R^2$, $R^{2'}$, $R^3$, $R^{3'}$, $R^4$, and/or $R^{4'}$ as described above.

Alternatively, the suitably substituted cyclohexanone derivative is first reduced to alcohol and this can then be dehydrated to cycloalkene. By 1,2-addition of sodium azide to the C=C double binding the corresponding diazide is synthesized and it is then reduced to diamine using hydrogen on the Lindlar catalyst.

The diamine(dichloro)platinum (II) compounds obtained after the reaction of the previously described diaminocyclohexane ligands with $K_2[PtCl_4]$ can then be converted into the corresponding diaqua(diamine) or aqua(sulphato) compounds in each case by using silver nitrate or silver sulphate. After the addition of oxalic acid or sodium oxalate the compounds according to the invention are obtained as isomer mixtures as illustrated for example in the following Diagram 2.

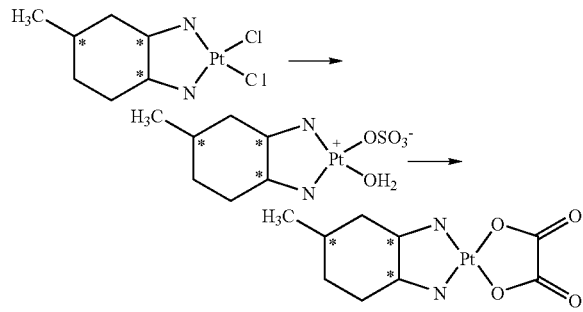

Diagram 2

Instead of substitution with methyl the substituents $R^1$, $R^{1'}$, $R^2$, $R^{2'}$, $R^3$, $R^{3'}$, $R^4$, and $R^{4'}$ can also be present as described above.

After the production of the compounds according to the invention as isomer mixtures, they can be separated into the pure isomers according to known methods. The racemic compound splitting preferably occurs at the stage of the diamines according to a known method such as the formation of diastereomer salts with chiralic acids or column chromatography on the chiralic stationary phase.

The invention also relates to compounds of the formula (I) as therapeutic or prophylactic agents. In addition, the invention relates to the application of a compound of the formula (I) for the manufacture of a medicament for the treatment and/or prophylaxis of tumor diseases.

Furthermore, the object of this invention is solved by a medicament, in particular for the therapy and/or prophylaxis of tumor diseases, which comprises the compound according to the invention. One of the uses of the compound according to the invention is for the prophylaxis and/or treatment of cancer diseases.

In the following, the medicament containing a compound according to the invention is described in more detail.

The medicament according to the invention is primarily administered intravenously, but also intramuscularly, intraperitoneally, subcutaneously or perorally. External application is also possible. Preferably, it is administered by intravenous injection or by intravenous infusion.

The medicament is manufactured according to known methods, wherein the compound according to the invention is used as such or in combination with suitable pharmaceutical carrier substances. If the medicament according to the invention contains pharmaceutical carrier substances as well as the active substance, the content of active substance in this mixture is 0.1 to 99.5, preferably 0.5 to 95% by weight of the total mixture.

The medicament according to the invention can be applied in any suitable formulation with the prerequisite that the establishment and maintenance of a sufficient level of active substance is ensured. This can be achieved, for example, by the oral or parenteral administration in suitable doses. Advantageously, the pharmaceutical preparation of the active substance is provided in the form of standard doses which are matched to the desired administration. A standard dose can be, for example, a tablet, a coated tablet, capsule, suppository or a measured volume of a powder, granulate, solution, emulsion or suspension.

A "standard dose" for the purposes of this invention is taken to mean a physically determined unit which contains an individual quantity of the active constituent in combination with a pharmaceutical carrier substance and its content of active substance corresponds to a fraction or multiple of a therapeutic single dose. A single dose preferably contains the quantity of active substance which is administered during an application and which normally corresponds to a whole, half, third or quarter of the daily dose. If only a fraction, such as half or quarter of the standard dose is needed for a single therapeutically administered dose, then the standard dose is advantageously divisible, e.g. in the form of a tablet with a dividing groove.

The medicaments according to the invention can, if the active substance is present in standard doses and is intended for application, e.g. on persons, contain about 0.1 to 500 mg, preferably 10 to 200 mg and particularly 50 to 150 mg of active substance.

Generally in human medicine, the active substance(s) are administered in a daily dose of 0.1 to 5, preferably 1 to 3 mg/kg of body weight, optionally in the form of a number, preferably 1 to 3, of single intakes for achieving the desired results. A single intake contains the active substance(s) in quantities of 0.1 to 5, preferably 1 to 3 mg/kg of body weight. With oral treatment similar dosages can be applied.

The therapeutic administration of the medicament according to the invention can occur 1 to 4 times daily at specified or varying time points, e.g. in each case before meals and/or in the evening. However, it may be necessary to deviate from the quoted dosages depending on the type, body weight and age of the individual to be treated, the type and severity of the disease, the type of preparation and the application of the medicament as well as the time period or interval within which the administration occurs. Consequently, in some cases it may be sufficient to use less than the amount of active substance mentioned above, whereas in other cases the above listed quantity of active substance must be exceeded. It may also be practicable to administer the medicaments only once or at intervals of a number of days.

The specification of the necessary optimum dosage and type of application of the active substance can be made by any specialist based on his specialist knowledge.

The medicaments according to the invention normally comprise the compounds according to the invention and non-toxic, pharmaceutically compatible medicament carriers, which as additive or dilution medium, are employed, for example, in solid, semi-solid or liquid form or as a means of enclosure, for example in the form of a capsule, a tablet coating, a bag or another container for the therapeutically active constituent. A carrier material may, for example, act as an intermediary for the ingestion of the medicament by the body, as a formulation medicament, sweetener, taste modifier, colorant or as a preservative.

For oral application, for example, tablets, coated tablets, hard and soft capsules, for example of gelatine, dispersible powder, granulate, aqueous and oily suspensions, emulsions, solutions and syrups can be employed.

Tablets may contain inert dilution agents, e.g. calcium carbonate, calcium phosphate, sodium phosphate or lactose; granulation and distribution agents, e.g. maize starch or alginates; binding agents, e.g. starches, gelatine or arabine; and lubricating agents, e.g. aluminium or magnesium stearate, talc or silicone oil. They can additionally be provided with a coating which is produced such that it causes delayed release and resorption of the medicament in the gastrointestinal tract, so that, for example, improved compatibility, assimilation or retardation is achieved. Gelatine capsules may contain the pharmaceutical substance mixed with a solid, e.g. calcium carbonate or kaolin or an oily dilution agent, e.g. olive, peanut or paraffin oil.

Aqueous suspensions may contain suspension agents, e.g. sodium carboxymethyl cellulose, methyl cellulose, hydroxypropyl cellulose, sodium alginate, polyvinyl pyrrolidon, traganth rubber or arabine; dispersant and wetting agents, e.g. polyoxyethylene stearate, heptadeca-ethylene-oxycatanol, polyoxyethylene sorbitol-monooleate, or lecithin; preservatives, e.g. methyl- or propylhydroxy-benzoate; taste modifiers; sweeteners, e.g. saccharose, lactose, sodium cyclamate, dextrose, invert sugar syrup.

Oily suspensions may contain, for example, peanut, olive, sesame, coconut or paraffin oil and thickening agents, such as bees wax, high melting point wax or cetyl alcohol; also sweeteners, taste modifiers and antioxidants.

Powder and granulates dispersible in water may contain the compound according to the invention in a mixture with dispersing, wetting and suspension agents, e.g. those mentioned above as well as with sweeteners, taste modifiers and colorants.

Emulsions may, for example, contain olive, peanut or paraffin oil as well as emulsifying agents such as arabine, traganth rubber, phosphatides, sorbitan monooleate, polyoxyethylene sorbitan monooleate and sweeteners and taste modifiers.

Aqueous solutions may contain preservatives, e.g. methyl- or propylhydroxybenzoates; thickening agents; taste modifiers; sweeteners, e.g. saccharose, lactose, sodium cyclamate, dextrose, invert sugar syrup as well as taste modifiers and colorants.

For the parenteral application of pharmaceutical substances sterile injectable aqueous solutions, isotonic salt solutions or other solutions can be used.

This invention also relates to a method for the prophylactic and/or therapeutic treatment of a mammal, which needs such a treatment, by administering a compound according to the invention. The mammal is selected from the group consisting of human beings and animals. Preferably the mammal requires treatment against a tumor disease as described above.

The invention is now explained in more detail based on examples.

SYNTHESIS EXAMPLE 1

2-bromine-4-methyl-cyclohexanone

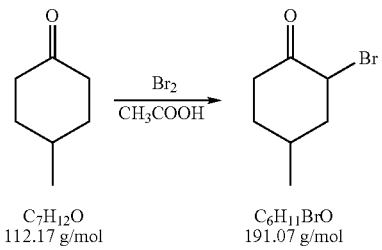

C$_7$H$_{12}$O
112.17 g/mol

C$_6$H$_{11}$BrO
191.07 g/mol

Preparation:

50 g=0.446 mmol 4-methylcyclohexanone 74 g=0.463 mmol bromine 92 ml 99% acetic acid 50 g 4-methylcyclohexanone are put into a two-necked flask with a separating funnel and Liebig condenser with 120 ml water, 92 ml 99% acetic acid and 2 drops of bromine. The reaction mixture is heated to about 50° C. until the reaction starts. Then 74 g bromine are added drop by drop over a period of 2 hours so slowly that the temperature remains at 35–40° C. Then the solution is neutralized with solid Na$_2$CO$_3$, so that the bromine ketone separates as a yellow oily liquid. The organic phase is washed with diluted Na$_2$CO$_3$ solution and then with water. The product is dried and filtered with Na$_2$SO$_4$.

Appearance:
  yellow oily liquid

Yield:
  33.3 g=0.174 mmol=39% (references: 78%)

α-bromine ketones decompose very easily during storage or heating, so that purification and characterization were omitted. By-products do not affect the isolation of the dioxime.

SYNTHESIS EXAMPLE 2

4-methylcyclohexane-1,2-dioxime

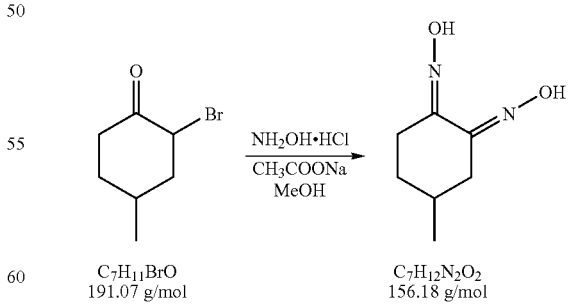

C$_7$H$_{11}$BrO
191.07 g/mol

C$_7$H$_{12}$N$_2$O$_2$
156.18 g/mol

Preparation:

33.2 g=0.174 mol 2-bromine-4-methyl-cyclohexanone 70.4 g=1.01 mol hydroxylaminohydrochloride 145.3 g sodium acetate trihydrate 126 ml methanol 70.4 g hydroxylaminohydrochloride and 145.3 g sodium acetate trihydrate are heated to boiling point in 126 ml methanol and 146 ml water. 33.2 g 2-bromine-4-methyl-cyclohexanone are dropped into the boiling solution over a period of 1.5 hours. Then boiling takes place for one hour under reflux and then about 100 ml of methanol is distilled off until the remaining solution becomes turbid. The residue is cooled to room temperature and then extracted three times with 80 ml benzene in each case. The combined benzene phases are added to about 500 ml of petroleum ether (boiling point 40–60° C.) and cooled for 2 days at 4° C. On the bottom a brown oil is deposited which after decanting the supernatant solution, recrystallizes in water. Through the use of a continuous extraction apparatus, the yield could be increased to 14% with further preparations.

Appearance:
  white solid

Yield:
  2 g=0.013 mol=7.5% (references: 25%)

NMR spectra: $^1$H-NMR spectrum in methanol-d4: δ=1.06 [d, 3H, CH$_3$, $^3J_{H,H}$=6.53 Hz], 1.26 [m, 1H], 1.74 [m, 1H], 1.82 [m, 1H], 1.98 [m, 1H], 2.37 [m, 1H], 2.97 [m, 2H]. $^{13}$C-NMR spectrum in methanol-d4: δ=20.8 [CH$_3$], 23.9 [CH$_2$], 29.2 [CH], 30.4 [CH$_2$ ], 33.0 [CH$_2$ ], 153.1 [C=NOH], 153.1 [C=NOH].

SYNTHESIS EXAMPLE 3

4-methyl-trans-cyclohexane-1,2-diaminodihydrogen-sulphate

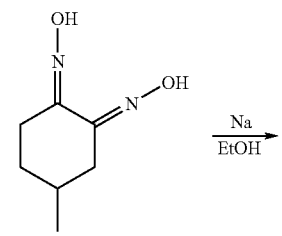

C$_7$H$_{12}$N$_2$O$_2$
156.18 g/mol

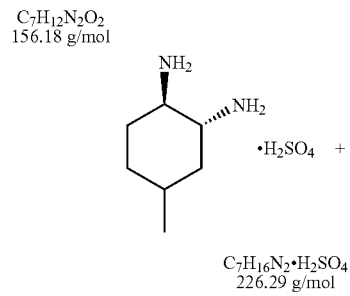

C$_7$H$_{16}$N$_2$·H$_2$SO$_4$
226.29 g/mol

Preparation:

4 g=0.026 mol 4-methylcyclohexane-1,2-dioxime 30 g=1.305 mol sodium 100 ml ethanol absolute 4 g 4-methylcyclohexane-1,2-dioxime are dissolved in a 1l three-necked flask with reflux condenser under N$_2$ atmosphere in 100 ml absolute ethanol and heated to boiling point. 30 g sodium are added in small pieces so that finally a large ball of molten sodium is formed on the liquid surface. A covering of sodium ethanolate on the surface of the ball is removed by further addition of absolute ethanol. The reaction mixture is boiled until all the sodium is dissolved. The solution is distilled with water vapor to first remove the alcohol and then to obtain the amine. The end of the distillation is reached when the distillate is no longer alkaline. The fraction containing the amine is acidified with 3 M sulphuric acid and evaporated to dryness on the rotary evaporator. The pink colored raw product is heated with 40 ml of ethanol under stirring to 50° C., the pink by-product dissolves and the white 4-methyl-trans-cyclohexane-1,2-diaminodihydrogensulphate is drawn off via a G4 filter crucible and dried in the air.

Appearance:
  white solid

Yield:
  3.067 g=0.013 mol=52%=(references: 78%)

| Elementary analysis: calculated for C$_7$H$_{16}$N$_2$.H$_2$SO$_4$ 226.29 g/mol | | | | | |
|---|---|---|---|---|---|
| | C | H | N | O | S |
| calculated: | 37.15 | 8.02 | 12.38 | 28.28 | 14.17 |
| found: | 37.2 | 77.80 | 12.17 | | |

IR spectrum [370–7000 cm$^{-1}$, CsI], characteristic bands (in cm$^{-1}$):

| in the range 2200–3300 | ν(N—H) |
|---|---|
| 1651 | δ(N—H) |
| 1550 | δ(N—H) |

NMR spectra:

Two isomers were found. The isomer with the lower concentration is designated with:

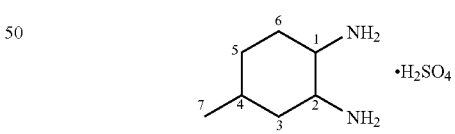

$^1$H-NMR spectrum in D$_2$O: δ=0.85 [d, 3H, H(7), $^3J_{H,H}$=6.53 Hz], 0.90 [d, 3H, H(7'), $^3J_{H,H}$=7.03 Hz], 0.99 [m, 1H, H(5)], 1.15 [m, 1H, H(3)], 1.42–1.55 [m, 2H, H(4), H(6)], 1.66–1.77 [m, 1H, H(5)], 1.99–2.10 [m, 2H, H(6) and H(3)], 3.23–3.39 [m, 2H, H(1) and H(2)], 3.50–360 [m, 2H, H(1') and H(2')].

$^{13}$C-NMR spectrum in D$_2$O: δ=17.9 [C(7')], 20.7 [C(7)], 24.0 [C(6')], 25.8 [C(4')], 27.8 [C(5')], 29.5 [C(6)], 30.2 [C(4)], 31.5 [C(5)], 33.8 [C(3')], 37.6 [C(3)], 48.7 [C(1' or 2')], 51.2 [C(1' or 2')], 52.4 [C(1 or 2)], 52.5 [C(1 or 2)].

SYNTHESIS EXAMPLE 4

2-bromine-4-ethyl-cyclohexanone

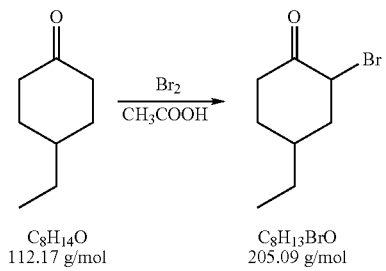

C$_8$H$_{14}$O
112.17 g/mol

C$_8$H$_{13}$BrO
205.09 g/mol

Preparation:

46 g=0.36 mmol 4-ethylcyclohexanone 66 g=0.37 mmol bromine 82 ml 99% acetic acid 46 g 4-ethylcyclohexanone are placed into a two-neck flask with separating funnel and Liebig condenser with 106 ml water, 82 ml 99% acetic acid and 2 drops of bromine. The reaction mixture is heated to about 50° C. until the reaction starts. Then 59.2 g bromine are added drop by drop over a period of 1.5 hours so slowly that the temperature remains at 35–40° C. Then the solution is neutralized with solid NaCO$_3$, so that the bromine ketone separates as a yellow oily liquid. The organic phase is washed with diluted NaCO$_3$ solution and then with water. The product is filtered over Na$_2$SO$_4$.

Appearance:
 yellow liquid

Yield:
 54 g=0.263 mol=73%

α-bromine ketones decompose very easily during storage or heating, so that purification and characterization were omitted. By-products do not affect the isolation of the dioxime.

SYNTHESIS EXAMPLE 5

4-ethylcyclohexane-1,2-dioxime

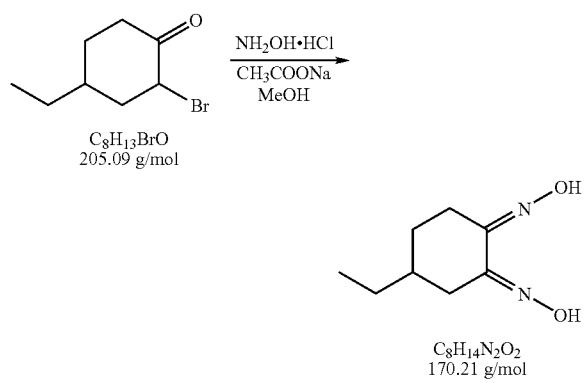

C$_8$H$_{13}$BrO
205.09 g/mol

C$_8$H$_{14}$N$_2$O$_2$
170.21 g/mol

Preparation:

54 g=0.263 mol 2-bromine-4-ethyl-cyclohexanone 105.7 g=1.52 mol hydroxylaminohydrochloride 212 g sodium acetate trihydrate 185 ml methanol 105.7 g hydroxylaminohydrochloride and 212 g sodium acetate trihydrate are heated to boiling point in 185 ml methanol and 185 ml water. 54 g 1-bromine-4-ethyl-cyclohexanone are dropped into the boiling solution over a period of one hour. Then boiling takes place for one hour under reflux and then distillation until the remaining solution becomes turbid. The residue is cooled to room temperature and then extracted with about 150 ml of benzene in a continuous extraction apparatus (in 4 portions of 100 ml, each for 2 hours). The benzene solution is topped up with petroleum ether (boiling point 40–60° C.) to about 900 ml and cooled overnight at 4° C. On the bottom a brown oil is deposited which after decanting the remaining solution, is recrystallized in water repeatedly until the white 4-ethylcyclohexane-1,2-dioxime is obtained (4–5 times).

Appearance:
 white laminar shaped solid

Yield: 11.9 g=0.0699 mol=26.6%

NMR spectra:
 $^1$H-NMR spectrum in methanol-d4:
 δ=0.98 [t, 3H, CH$_3$, $^3J_{H,H}$=7.53 Hz], 1.25 [m, 1H], 1.40 [m, 2H, CH$_2$CH$_3$], 1.50 [m, 1H], 1.88 [m, 1H], 2.03 [m, 1H], 2.37 [m, 1H], 2.96 [m, 2H].
 $^{13}$C-NMR spectrum in methanol-d4: δ=10.73 [CH$_3$], 23.9 [CH$_2$], 27.9 [CH$_2$], 28.8 [CH$_2$], 30.8 [CH$_2$], 35.9 [CH], 153.3 [C=NOH], 153.5 [C=NOH].

SYNTHESIS EXAMPLE 6

4-ethyl-trans-cyclohexane-1,2-diaminodihydrogen-sulphate

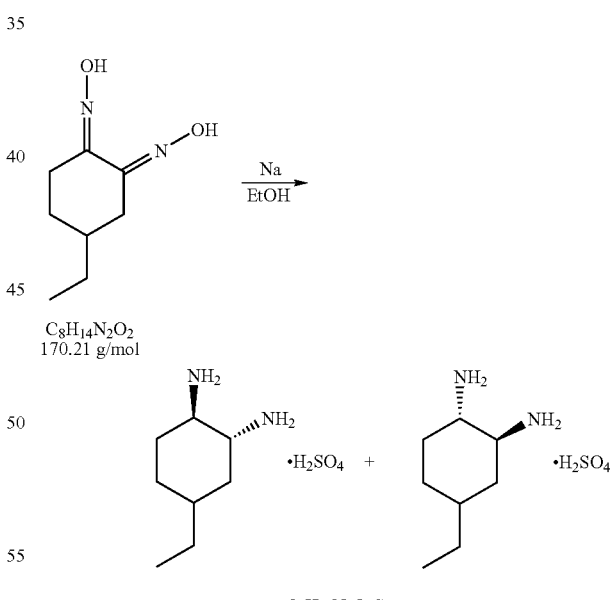

C$_8$H$_{14}$N$_2$O$_2$
170.21 g/mol

C$_8$H$_{20}$N$_2$O$_4$S
240.32 g/mol

Preparation:

9 g=0.053 mol 4-ethylcyclohexane-1,2-dioxime 50.05 g=2.20 mol sodium 280 ml ethanol absolute 9 g 4-ethylcyclohexane-1,2-dioxime are dissolved in a 1 l three-necked flask with reflux condenser under N$_2$ atmosphere in 100 ml absolute ethanol and heated to boiling point. 50.5 g sodium are added in small pieces so that finally a large ball of molten sodium is formed on the liquid surface. A covering of sodium ethanolate on the surface of the ball is removed by further addition of absolute ethanol. The reaction mixture is boiled until all the sodium is dissolved. The solution is distilled with water vapor to first remove the alcohol and then to obtain the amine. The end of the distillation is reached when the distillate is no longer alkali. The fraction containing the amine is acidified with 3 M sulphuric acid and evaporated to dryness on the rotary evaporator. The pink colored raw product is heated with 40 ml of ethanol under stirring to 50° C., the pink by-product dissolves and the white 4-ethyl-trans-cyclohexane-1,2-diaminodihydrogensulphate is drawn off via a G4 filter crucible and dried in the air.

Appearance:
  white solid

Yield:
  3.055 g=0.013 mol=16%

Elementary analysis: calculated for $C_8H_{20}N_2 \cdot H_2SO_4$ 240.32 g/mol

|  | C | H | N | O | S |
|---|---|---|---|---|---|
| calculated: | 39.98 | 8.39 | 11.66 | 26.63 | 13.34 |
| found: | 40.11 | 8.10 | 11.64 |  |  |

IR spectrum [370–7000 cm$^{-1}$, CsI], characteristic bands (in cm$^{-1}$):

| in the range 2200–3300 | ν(N—H) |
| 1637 | δ(N—H) |
| 1546 | δ(N—H) |

SYNTHESIS EXAMPLE 7

(SP-4-3)-dichloro(4-methyl-trans-cyclohexane-1,2-diamine)platinum (II)

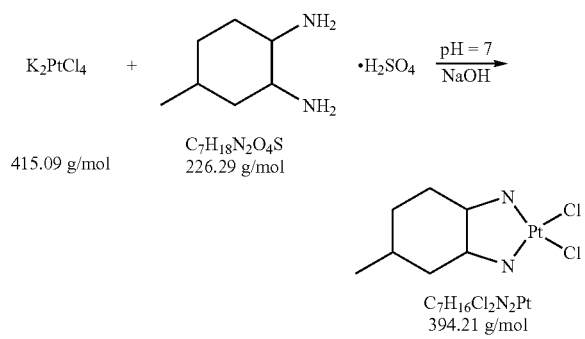

Preparation:
  2.15 g=9.50 mmol 4-methyl-trans-cyclohexane-1,2-diaminodihydrogensulphate 3.944 g=9.50 mmol $K_2PtCl_4$ 3.944 g of $K_2PtCl_4$ are dissolved in 50 ml tridistilled water and suspended with 2.15 g 4-methyl-trans-cyclohexane-1,2-diaminodihydrogensulphate. Then the pH value is set to 7 with 0.5 M NaOH and maintained at this value with a 718 Stat Titrino from Methrom with 0.1 M NaOH. The voluminous yellow precipitate is drawn off through a G4 filter crucible, washed twice each with ice-cold tridistilled water and ethanol and dried in the vacuum desiccator over phosphorus pentoxide.

Appearance:
  yellow solid

Melting point:
  >310° C. decomposition

Yield:
  3.0 g=7.6 mmol=80%

Elementary analysis: calculated for $C_7H_{16}Cl_2N_2Pt$ 394.21 g/mol

|  | C | H | N | Cl | Pt |
|---|---|---|---|---|---|
| calculated: | 21.33 | 4.09 | 7.11 | 17.99 | 49.49 |
| found: | 21.44 | 3.80 | 7.00 |  |  |

IR spectrum [370–7000 cm$^{-1}$, CsI], characteristic bands (in cm$^{-1}$):

| 3273, 3197 | ν(N—H) |
| 2936, 2866 | ν(C—H) |
| 1562 | δ(N—H) |

SYNTHESIS EXAMPLE 8

(SP-4-3)-dichloro(4-ethyl-trans-cyclohexane-1,2-diamino)platinum (II)

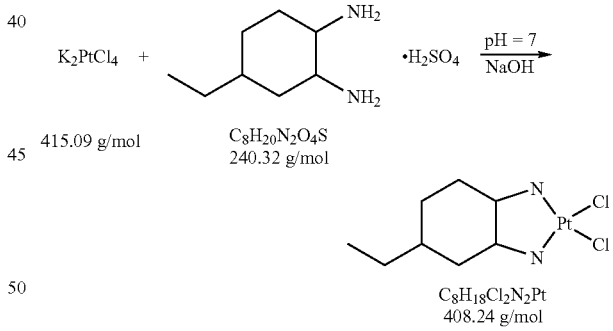

Preparation:
  2.000 g=8.32 mmol 4-ethyl-trans-cyclohexane-1,2-diaminodihydrogensulphate
  3.454 g=8.32 mmol $K_2PtCl_4$
  3.454 g $K_2PtCl_4$ are dissolved in 50 ml tridistilled water and suspended with 2.000 g 4-ethyl-trans-cyclohexane-1,2-diaminodihydrogensulphate. Then the pH value is set to 7 with 0.5 M NaOH and maintained at this value with a 718 Stat Titrino from Methrom with 0.1 M NaOH. The voluminous yellow precipitate is drawn off through a G4 filter crucible, washed twice each with ice-cold tridistilled water and ethanol and dried in the vacuum desiccator over phosphorus pentoxide.

Appearance:
yellow solid

Melting point:
>310° C. decomposition

Yield:
3.238 g=7.93 mmol=95%

| Elementary analysis: calculated for $C_8H_{18}Cl_2N_2Pt$ 408.24 g/mol | | | | | |
|---|---|---|---|---|---|
| | C | H | N | Cl | Pt |
| calculated: | 23.54 | 4.44 | 6.86 | 17.37 | 47.79 |
| found: | 23.52 | 4.18 | 6.63 | | |

IR spectrum [370–7000 cm$^{-1}$, CsI], characteristic bands (in cm$^{-1}$): 3273, 3196ν(N—H) 2933, 2861ν(C—H) 1558δ (N—H)

SYNTHESIS EXAMPLE 9

4,5-dimethyl-1-cyclohexene (2 ways: mesylate/tosylate)

4,5-di(hydroxymethyl)cyclohexene

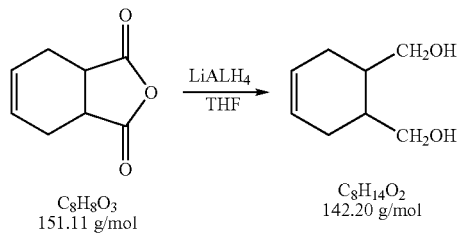

$C_8H_8O_3$
151.11 g/mol $C_8H_{14}O_2$
142.20 g/mol

Preparation:
30 g=0.2 mol cis-1,2,3,6-tetrahydrophtalic acid anhydride 45 g=1.2 mol LiAlH$_4$ 375 ml abs. tetrahydrofuran 30 g cis-1,2,3,6-tetrahydrophtalic acid anhydride in 150 ml abs. THF are added through a separating funnel to a solution of 45 g lithium aluminum hydride in 900 ml abs. THF and heated for 48 hours under reflux. Then the mixture is first cooled to room temperature and then in an ice-brine bath to about 15° C. and the unused portion of the hydride is carefully broken down with water. Through the addition of diluted sulphuric acid the salts are dissolved and through the addition of diethylether the organic phase is separated from the aqueous phase.

The organic phase is washed with a saturated Na$_2$CO$_3$ solution and dried with Na$_2$SO$_4$. The solvents, i.e. ether and THF are centrifuged off in a vacuum.

Appearance:
yellow oily liquid

Yield:
27 g=0.19 mol=95.6%

SYNTHESIS EXAMPLE 10

4,5-di(methylsulphonate)cyclohexene

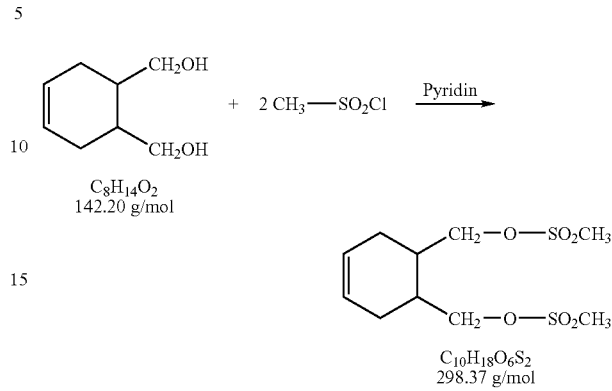

$C_8H_{14}O_2$
142.20 g/mol $C_{10}H_{18}O_6S_2$
298.37 g/mol

Preparation:
28 g=0.19 mol 4,5-di(hydroxymethyl)-1-cyclohexene 46 g=0.40 mol methane sulphochloride (Mr=114.55) 330 ml abs. pyridine 46 g methane sulphochloride are added in small portions to a cold solution of 28 g 4,5-di(hydroxymethyl)-1-cyclohexene in 200 ml abs. pyridine. The mixture is stirred for 4–5 hours at a temperature of 3–4° C. and then stored for a further 24 hours at 2° C. After the addition of an excess of diluted hydrochloric acid, the solution is extracted with chloroform. The chloroform phase is washed with a saturated Na$_2$CO$_3$ solution and water, dried with Na$_2$SO$_4$ and the solvent centrifuged off in a vacuum. The product is then recrystallised out of methanol and petroleum spirit (40–60° C.).

Appearance:
colorless crystals

M.p.:
86–87° C.

Yield:
39 g=0.13 mol=68.8%

| Elementary analysis: calculated for $C_{10}H_{18}S_2O_6$ | | | | |
|---|---|---|---|---|
| | C | H | O | S |
| calculated: | 40.26 | 6.08 | 32.17 | 21.49 |
| found: | 40.17 | 6.08 | | 21.42 |

SYNTHESIS EXAMPLE 11

4,5-di(methyltosylate)cyclohexene

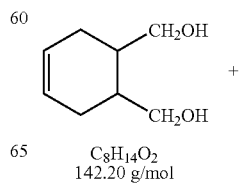

$C_8H_{14}O_2$
142.20 g/mol

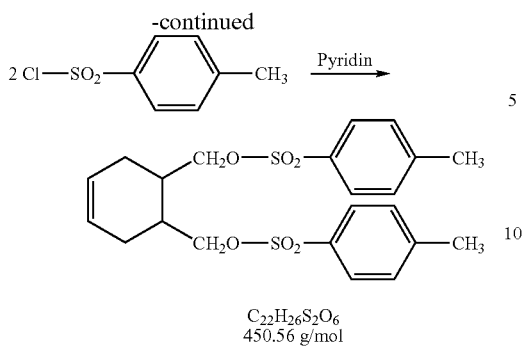

C$_{22}$H$_{26}$S$_2$O$_6$
450.56 g/mol

Preparation:

30 g=0.21 mol 4,5-di(hydroxymethyl)-1-cyclohexene 84 g=0.44 mol p-toluol-4-sulphochloride (Mr=190.65) 300 ml abs. pyridine 84 g p-toluol-4-sulphochloride in 200 ml pyridine are added in small portions to a cold solution of 30 g 4,5-di(hydroxymethyl)-1-cyclohexene in 60 ml abs. pyridine.

The mixture is stirred for 4–5 hours at a temperature of 3–4° C. and then stored for a further 24 hours at 2° C. On the next day the mixture is mixed with 90 ml concentrated HCl and 180 ml ice, whereby a brown oil is formed. The aqueous phase is extracted twice with 50 ml ether. The ether phases and the ditosylate are washed once with water and then with a saturated NaHCO$_3$ solution and then again with water. The ether phase is dried with Na$_2$SO$_4$ and the solvent centrifuged off in a vacuum.

Appearance:

colorless crystals

M.p.:

93–94° C.

Yield:

49 g=0.11 mol=52.4%

Elementary analysis: calculated for C$_{22}$H$_{26}$S$_2$O$_6$

|  | C | H | O | S |
|---|---|---|---|---|
| calculated: | 58.65 | 5.82 | 21.31 | 14.23 |
| found: | 58.06 | 5.84 |  | 13.91 |

SYNTHESIS EXAMPLE 12

4,5-dimethyl-1-cyclohexene from the di(methylsulphonate)

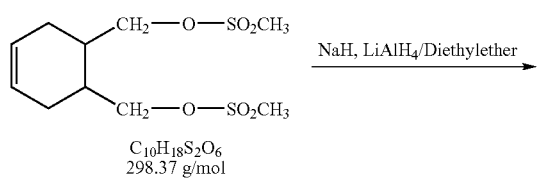

C$_{10}$H$_{18}$S$_2$O$_6$
298.37 g/mol

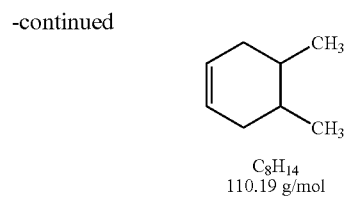

C$_8$H$_{14}$
110.19 g/mol

Preparation:

19.0 g=0.064 mol 4,5-di(methane sulphonate)cyclohexene 10.6 g=0.28 mol LiAlH$_4$ 6.40 g=0.27 mol NaH 11.2 g LiAlH$_4$ and 6.7 g NaH in 300 ml abs. ether are heated for 30 min. under reflux and then cooled to −5° C. 19 g of the dimesylate are added in solid form and the temperature maintained at −5° C. for one hour. Then the mixture is heated overnight under reflux.

The hydride excesses are broken down by the addition of saturated ammonium chloride solution and the mixture is stirred for one hour. Then the solid is filtered off and washed with ether. The organic phase is dried with Na$_2$SO$_4$ and ether is centrifuged off. Then the product is distilled off at 123–125° C.

Appearance:

colorless oily liquid

Yield:

2.3 g=20.9 mmol=32.6%

SYNTHESIS EXAMPLE 13

4,5-dimethyl-1-cyclohexene from the di(methyltosylate)

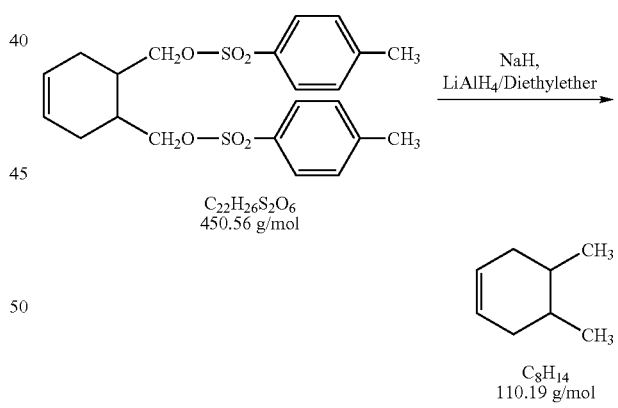

C$_{22}$H$_{26}$S$_2$O$_6$
450.56 g/mol

C$_8$H$_{14}$
110.19 g/mol

Preparation:

48.0 g=0.1 mol 4,5-di(methyltosylate)cyclohexene 17.0 g=0.44 mol LiAlH$_4$ 10.0 g=0.42 mol NaH 17 g LiAlH$_4$ and 10 g NaH in 500 ml abs. ether are heated for 30 min under reflux and then cooled to −5° C. 48 g of the ditosylate are added in solid form and the temperature maintained at −5° C. for one hour. Then the mixture is heated overnight under reflux.

The hydride excesses are broken down by the addition of saturated ammonium chloride solution and the mixture is stirred for one hour. Then the solid is filtered off and washed with ether. The organic phase is dried with Na$_2$SO$_4$ and ether is centrifuged off. Then the product is distilled off at 123–125° C.

Appearance:
colorless oily liquid

Yield:
2.3 g=20.9 mmol=20.9%

SYNTHESIS EXAMPLE 14

4,5-dimethyl-cyclohexane-1,2-diazide

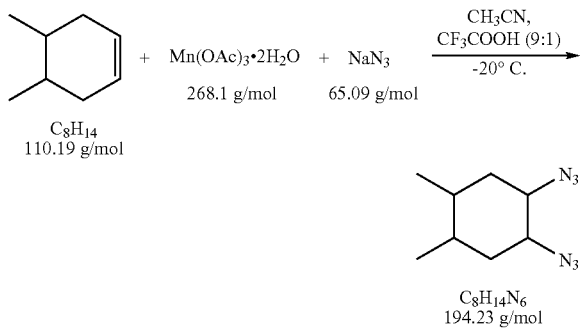

Preparation:
1.90 g=17.2 mmol 4,5-dimethyl-1-cyclohexene 13.9 g=51.6 mmol Mn(OAc)$_3$.2H$_2$O 5.60 g=86.0 mmol NaN$_3$ 1.9 g 4,5-dimethyl-1-cyclohexene and 20 ml TFA are added at −20° C. and under a N$_2$-atmosphere to a suspension of Mn(OAc)$_3$.2H$_2$O and NaN$_3$ in 200 ml acetonitrile. The mixture is stirred for 90 min. at −19 to −21° C. and then diluted with a 10% NaHSO$_3$ solution. The solution is then extracted with 3×50 ml petroleum spirit (boiling point=40–60° C.).

The organic phases are washed with saturated Na$_2$CO$_3$ solution and then washed with saturated NaCl solution and dried with Na$_2$SO$_4$. The solution is then centrifuged off in a vacuum.

Yield:
2 g=10.3 mmol=60%

Appearance:
colorless liquid

SYNTHESIS EXAMPLE 15

4,5-dimethyl-cyclohexane-1,2-diamine

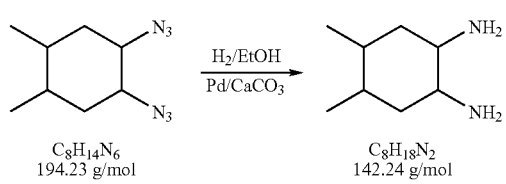

Preparation:
1.9 g=9.8 mmol 4,5-dimethyl-cyclohexane-1,2-diazide, 0.8 g Pd/CaCO$_3$ 1.9 g 4,5-dimethyl-cyclohexane-1,2-diazide in 60 ml abs. ethanol are mixed with 0.8 g Lindlar catalyst and reduced to diamine over 45 hours in an autoclave at a H$_2$ pressure of 3–3.5 bar. At the end of the reduction the catalyst is filtered off and the ethanol is centrifuged off in a vacuum.

Yield:
1.34 g=9.42 mmol=96% 4,5-dimethyl-1,2-cyclohexanediamine

Characterization as Dihydrogen Sulphate:
4,5-dimethyl-cyclohexane-1,2-diamine is acidified with sulphuric acid (c=3 mol/l). The precipitated solid is absorbed with ethanol and heated to 50° C. The impurities are dissolved and the white 4,5-dimethyl-1,2-diaminocyclohexane-dihydrogensulphate is drawn off via a G4 filter crucible and dried over phosphorus pentoxide in a vacuum.

| Elementary analysis: calculated for C$_8$H$_{18}$N$_2$.H$_2$SO$_4$ | | | | | |
|---|---|---|---|---|---|
| | C | H | N | O | S |
| calculated: | 39.98 | 8.39 | 11.66 | 26.63 | 13.34 |
| found: | 39.15 | 8.55 | 11.23 | | 13.43 |

NMR spectrum:

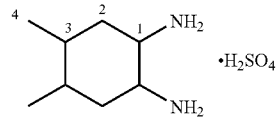

$^1$H-NMR in D$_2$O: δ=0.82–0.87 [m, 3H, H(4) and H(4'), $^3$J$_{H,H}$], 1.68 [m, 1H, H(3) and H(3')], 1.95 [m, 2H, H(2) and H(2')], 3.34–3.4 [m, 2H, H(1) and H(1')], 3.47–3.54 [m, 2H, H(2) and H(2')].

$^{13}$C-NMR spectrum in D$_2$O: δ=10.94 [C(4')], 18.21 [C(4)], 31.61 [C(2')], 31.67 [C(3')], 32.65 [C(3)], 36.55 [C(2)], 48.71 [C(1')], 52.82 [C(1)].

SYNTHESIS EXAMPLE 16

4-propyl-1-cyclohexene a) 4-propyl-1-cyclohexanol

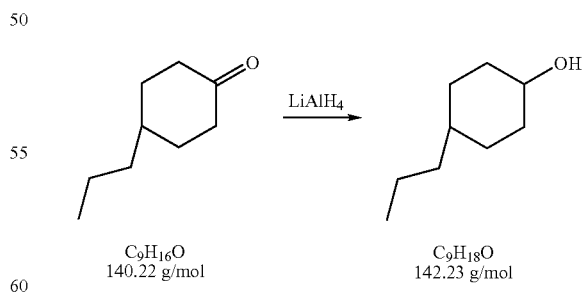

Preparation:
20 g=143 mmol 4-propyl-1-cyclohexanone 10 g LiAlH$_4$
20 g 4-1-cyclohexanone are added slowly drop by drop through a separating funnel and under an argon atmosphere to a cooled solution of 10 g LiAlH$_4$ in 500 ml abs. THF.

After the end of the addition the mixture is heated to reflux and stirred for 48 hours at this temperature. After the end of the reduction 500 ml diethylether are added and the unreacted residues of LiAlH₄ are broken down by the drop-by-drop addition of dest. water. Then the mixture is mixed with 200 ml 10% sulphuric acid to dissolve the inorganic salts. The ether phase is then separated and the aqueous phase extracted twice with 50 ml of ether. The combined ether phases are dried with Na₂SO₄, the ether and THF are centrifuged off.

Appearance:

colorless oily liquid

Yield:

19.3 g=135 mmol=94% b) 4-propyl-1-cyclohexene

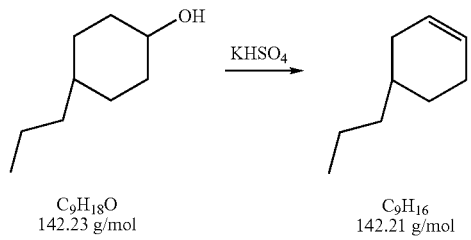

Preparation:

19.0 g=133 mmol 4-propylcyclohexanol 16.0 g KHSO₄

19 g 4-propyl-1-cyclohexanol are mixed with 16 g KHSO₄ and stirred for one week at 70° C. After the addition of ethylacetate KHSO₄ is filtered off. Ethylacetate is evaporated and the product obtained by fractional distillation.

Yield:

13.7 g=110 mmol=83%

Appearance:

colorless liquid

Boiling point=151–153° C.

Synthesis Example 17

4-propyl-cyclohexane-1,2-diazide

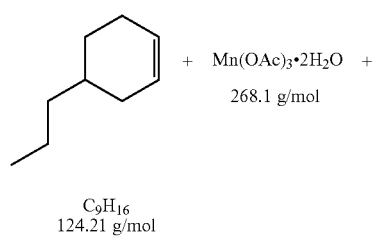

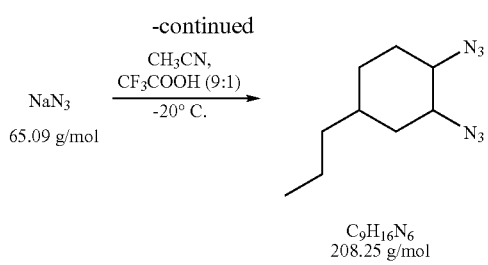

Preparation:

4.80 g=38.6 mmol 4-propyl-1-cyclohexene 31.1 g=116 mmol Mn(OAc)₃.2H₂O 12.6 g=196 mmol NaN₃

4.8 g 4-propyl-1-cyclohexene and 44 ml TFA are added at −20° C. and under N₂ atmosphere to a suspension of Mn(OAc)₃.2H₂O and NaN₃ in 440 ml acetonitrile. The mixture is stirred for 3 hours at −19 to −21° C. and then diluted with a 10% NaHSO₃ solution. The colorless solution is then extracted with 3×50 ml petroleum spirit (boiling point=40–60° C.).

The organic phases are washed with saturated Na₂CO₃ solution and then with saturated NaCl solution and dried with Na₂SO₄. The solution is then centrifuged off in a vacuum.

Yield:

29.4 g=163 mmol=78.5%

Appearance:

colorless liquid

SYNTHESIS EXAMPLE 18

4-propyl-trans-cyclohexane-1,2-diamine

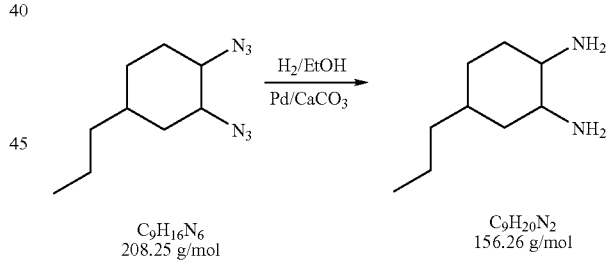

Preparation:

4 g=19.2 mmol 4-propyl-cyclohexane-1,2-diazide 1.6 g Pd/CaCO₃

4 g 4-ethyl-cyclohexane-1,2-diazide in 60 ml abs. ethanol are mixed with 1.6 g Lindlar catalyst and reduced to diamine over 48 hours in an autoclave at a H₂ pressure of 3 bar. At the end of the reduction the catalyst is filtered off and the ethanol is centrifuged off in a vacuum.

Characterization as dihydrogen sulphate:

4-propyl-1,2-diaminocyclohexane is acidified with sulphuric acid (c=3 mol/l). The precipitated solid is absorbed with ethanol and heated to 50° C. The impurities are dissolved and the white 4-propyl-cyclohexane-1,2-diamine-dihydrogensulphate is drawn off via a G4 filter crucible and dried over P₂O₅ in a vacuum.

SYNTHESIS EXAMPLE 19

4-t-butyl-1-cyclohexene

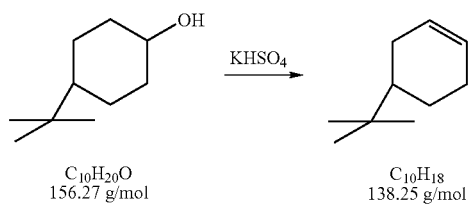

Preparation:

20.0 g=120 mmol 4-propylcyclohexanol 17.0 g KHSO$_4$ 20 g 4-t-butyl-1-cyclohexanol are mixed with 17 g KHSO$_4$ and stirred for one week at 95° C. After the addition of ethylacetate KHSO$_4$ is filtered off. Ethylacetate is evaporated and the product obtained by fractional distillation.

Yield:

11 g=80 mmol=65%

Appearance:

colorless liquid
Boiling point=168–171° C.

SYNTHESIS EXAMPLE 20

4-t-butyl-cyclohexane-1,2-diazide

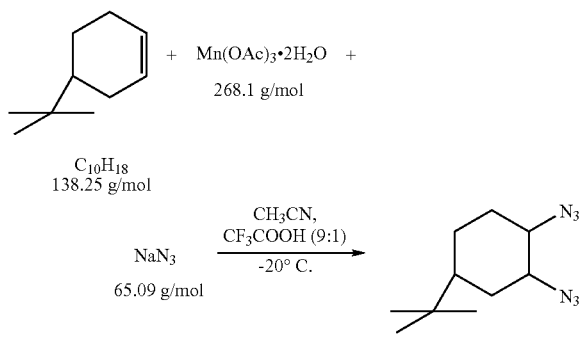

Preparation:

5.0 g=36 mmol 4-t-butyl-1-cyclohexene 29 g=108 mmol Mn(OAc)$_3$.2H$_2$O 11.8 g=180 mmol NaN$_3$ 5 g 4-t-butyl-1-cyclohexene and 42 ml TFA are added at −20° C. and under N$_2$ atmosphere to a suspension of Mn(OAc)$_3$.2H$_2$O and NaN$_3$ in 420 ml acetonitrile. The mixture is stirred for 3 hours at −19 to −21° C. and then diluted with a 10% NaHSO$_3$ solution. The colorless solution is then extracted with 3×50 ml petroleum spirit (boiling point=40–60° C.).

The organic phases are washed with saturated Na$_2$CO$_3$ solution and then washed with saturated NaCl solution and dried with Na$_2$SO$_4$. The solution is then centrifuged off in a vacuum.

Yield:

6.39 g=28.7 mmol=80%

Appearance:

colorless liquid

SYNTHESIS EXAMPLE 21

4-t-butyl-trans-cyclohexane-1,2-diamine

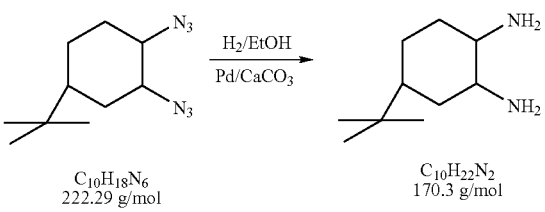

Preparation:

4 g=19.2 mmol 4-t-butyl-cyclohexane-1,2-diazide 1.6 g Pd/CaCO$_3$ 4 g 4-ethyl-cyclohexane-1,2-diazide in 60 ml abs. ethanol are mixed with 1.6 g Lindlar catalyst and reduced to diamine over 48 hours in an autoclave at a H$_2$ pressure of 3 bar. At the end of the reduction the catalyst is filtered off and the ethanol is centrifuged off in a vacuum.

Characterization as dihydrogen sulphate:

4-butyl-1,2-diaminocyclohexane is acidified with sulphuric acid (c=3 mol/l). The precipitated solid is absorbed with ethanol and heated to 50° C. The impurities are dissolved and the white 4-butyl-cyclohexane-1,2-diamine-dihydrogensulphate is drawn off via a G4 filter crucible and dried over P$_2$O$_5$ in a vacuum.

SYNTHESIS EXAMPLE 22

4-phenyl-1-cyclohexene a) 4-phenyl-1-cyclohexanol

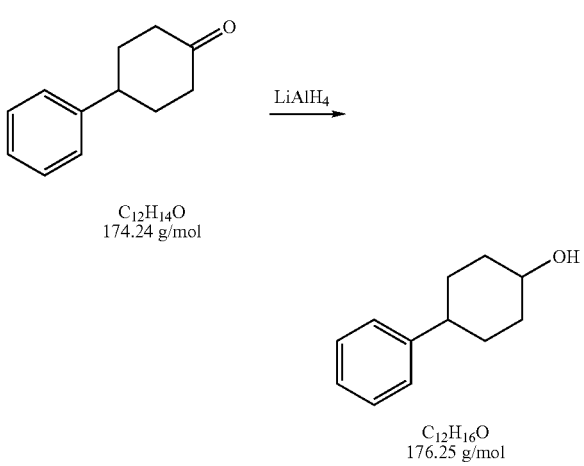

Preparation:

20 g=115 mmol 4-phenyl-1-cyclohexanone 10 g LiAlH$_4$ 20 g 4-phenyl-1-cyclohexanone are added slowly drop by drop through a separating funnel and under an argon atmosphere to a cooled solution of 10 g LiAlH$_4$ in 500 ml abs. THF.

After the end of the addition the mixture is heated to reflux and stirred for 48 hours at this temperature. After the end of the reduction 500 ml diethylether are added and the unreacted residues of LiAlH$_4$ are broken down by the drop-by-drop addition of dest. water. Then the mixture is mixed with 200 ml 10% sulphuric acid to dissolve the inorganic salts. The ether phase is then separated and the aqueous phase extracted twice with 50 ml of ether. The combined ether phases are dried with Na$_2$SO$_4$, the ether and THF are centrifuged off.

Appearance:
  white solid

Yield:
  18 g=102 mmol=89%

Melting point:
  100.5–114.1° C.

b) 4-phenyl-1-cyclohexene

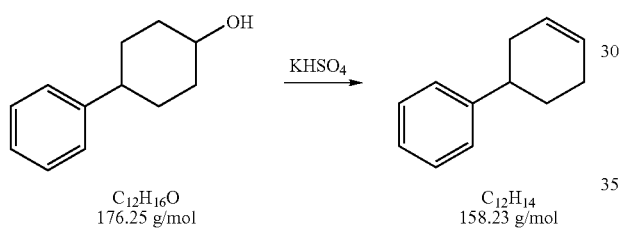

Preparation:

18.0 g=102 mmol 4-phenylcyclohexanol 16.0 g KHSO$_4$ 19 g 4-propyl-1-cyclohexanol are mixed with 16 g KHSO$_4$ and stirred for one week at 125° C. After the addition of ethylacetate KHSO$_4$ is filtered off. Ethylacetate is evaporated and the product obtained by vacuum distillation.

Yield:
  12 g=76 mmol=75%

Appearance:
  colorless liquid

Boiling point=56–59° C. at 1.1–1.3 mbar

Synthesis Example 23

4-phenyl-cyclohexane-1,2-diazide

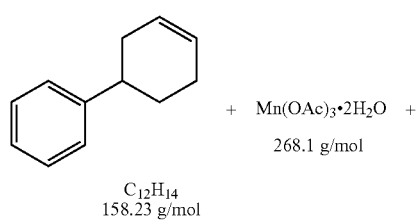

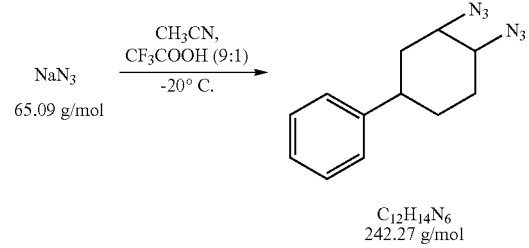

Preparation:

5.3 g=33.5 mmol 4-phenyl-1-cyclohexene 27 g=101 mmol Mn(OAc)$_3$.2H$_2$O 11 g=168 mmol NaH$_3$ 5.3 g 4-phenyl-1-cyclohexene and 40 ml TFA are added at −20° C. and under N$_2$ atmosphere to a suspension of Mn(OAc)$_3$.2H$_2$O and NaN$_3$ in 400 ml acetonitrile. The mixture is stirred for 3 hours at −19 to −21° C. and then diluted with a 10% NaHSO$_3$ solution. The colorless solution is then extracted with 3×50 ml petroleum spirit (boiling point=40–60° C.).

The organic phases are washed with saturated Na$_2$CO$_3$ solution and then with saturated NaCl solution and dried with Na$_2$SO$_4$. The solution is then centrifuged off in a vacuum.

Yield:
  6 g=24.8 mmol=74%

Appearance:
  colorless liquid

SYNTHESIS EXAMPLE 24

4-phenyl-trans-cyclohexane-1,2-diamine

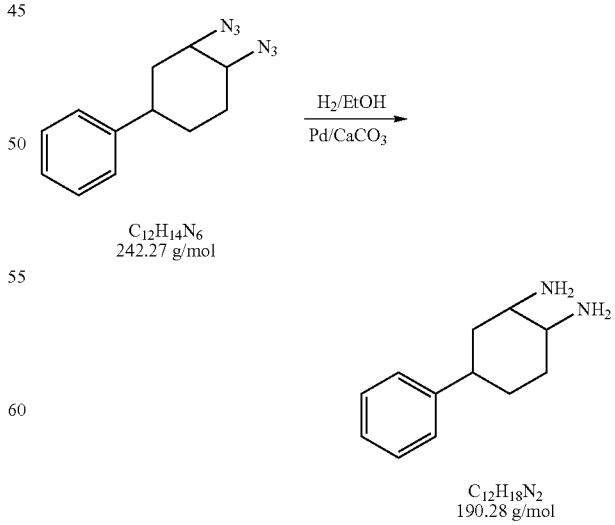

29

Preparation:

4 g=19.2 mmol 4-phenyl-cyclohexane-1,2-diazide 1.6 g Pd/CaCO$_3$ 4 g 4-phenyl-cyclohexane-1,2-diazide in 60 ml abs. ethanol are mixed with 1.6 g Lindlar catalyst and reduced to diamine over 48 hours in an autoclave at a H$_2$ pressure of 3 bar. At the end of the reduction the catalyst is filtered off and the ethanol is centrifuged off in a vacuum.

Characterization as dihydrogen sulphate:

4-phenyl-1,2-diaminocyclohexane is acidified with sulphuric acid (c=3 mol/l). The precipitated solid is absorbed with ethanol and heated to 50° C. The impurities are dissolved and the white 4-phenyl-cyclohexane-1,2-diamine-dihydrogensulphate is drawn off via a G4 filter crucible and dried over P$_2$O$_5$ in a vacuum.

SYNTHESIS EXAMPLE 25

(SP-4-3)-dichloro(4,5-dimethyl-trans-cyclohexane-1,2-diamine)platinum (II)

C$_8$H$_{18}$N$_2$
142.24 g/mol

+ K$_2$PtCl$_4$
415.09 g/mol

→

C$_8$H$_{18}$Cl$_2$N$_2$Pt
408.24 g/mol

Preparation:

0.60 g=4.22 mmol 4,5-dimethyl-trans-cyclohexane-1,2-diamine 1.75 g=4.22 mmol K$_2$PtCl$_4$ 1.75 g K$_2$PtCl$_4$ are dissolved in 30 ml tridistilled water and suspended with 0.6 g 4,5-dimethyl-trans-cyclohexane-1,2-diamine. The precipitate formed is drawn off gradually over a POR 4 glass filter crucible and dried in the desiccator over phosphorus pentoxide.

Appearance:

yellow solid

Yield:

1.12 g=2.74 mmol=65%

Elementary analysis: calculated for C$_8$H$_{18}$N$_2$Cl$_2$Pt 408.24 g/mol

|  | C | H | N | Pt | Cl |
|---|---|---|---|---|---|
| calculated: | 23.54 | 4.44 | 6.86 | 47.79 | 17.37 |
| found: | 23.32 | 4.39 | 6.59 | 47.00 | 16.81 |

30

SYNTHESIS EXAMPLE 26

(SP-4-3)-dichloro(4-propyl-trans-cyclohexane-1,2-diamine)platinum (II)

C$_9$H$_{20}$N$_2$·H$_2$SO$_4$
254.35 g/mol

+ K$_2$PtCl$_4$
415.09 g/mol

→

C$_9$H$_{20}$N$_2$Cl$_2$Pt
422.27 g/mol

Preparation:

1.53 g=6.02 mmol 4-propyl-trans-cyclohexane-1,2-diamine-dihydrogensulphate 2.50 g=6.02 mmol K$_2$PtCl$_4$ 2.5 g of K$_2$PtCl$_4$ are dissolved in 40 ml tridistilled water and suspended with 1.53 g 4-propyl-trans-cyclohexane-1,2-diamine-dihydrogensulphate. Then the pH value is set to 7 with 0.5 N NaOH and maintained at this value with 0.1 N NaOH, wherein the pH value is continuously measured with a pH meter. The precipitate formed is drawn off gradually over a POR 4 glass filter crucible and dried in the desiccator over phosphorus pentoxide.

Appearance:

yellow solid

Yield:

1.83 g=4.33 mmol=72%

SYNTHESIS EXAMPLE 27

(SP-4-3)-dichloro(4-t-butyl-trans-cyclohexane-1,2-diamine)platinum (II)

C$_{10}$H$_{22}$N$_2$·H$_2$SO$_4$
268.38 g/mol

+ K$_2$PtCl$_4$
415.09 g/mol

→

C$_{10}$H$_{22}$N$_2$Cl$_2$Pt
436.30 g/mol

Preparation:

1.60 g=6.02 mmol 4-t-butyl-trans-cyclohexane-1,2-diamine-dihydrogensulphate 2.50 g=6.02 mmol K$_2$PtCl$_4$ 2.5 g of K₂PtCl₄ are dissolved in 50 ml tridistilled water and suspended with 1.6 g 4-t-butyl-trans-cyclohexane-1,2-diamine-dihydrogensulphate. Then the pH value is set to 7 with 0.5 N NaOH and maintained at this value with 0.1 N NaOH, wherein the pH value is continuously measured with a pH meter. The precipitate formed is drawn off gradually over a POR 4 glass filter crucible and dried in the desiccator over phosphorus pentoxide.

Appearance:
  yellow solid

Yield:
  1.8 g=4.12 mmol=70%

SYNTHESIS EXAMPLE 28

(SP-4-3)-dichloro(4-phenyl-trans-cyclohexane-1,2-diamine)platinum (II)

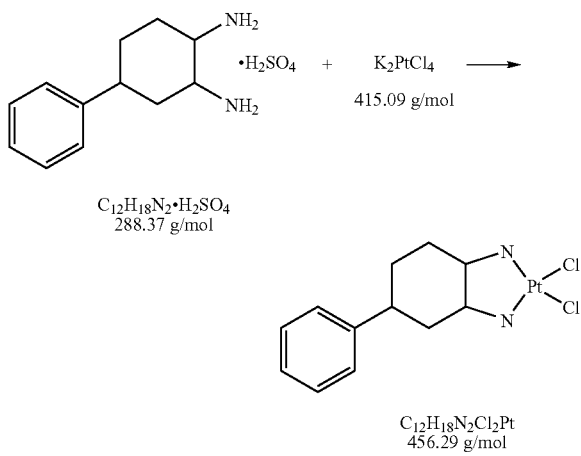

Preparation:
  1.4 g=4.82 mmol 4-phenyl-trans-cyclohexane-1,2-diamine-dihydrogensulphate 2.0 g=4.82 mmol K₂PtCl₄

2.0 g of K₂PtCl₄ are dissolved in 40 ml tridistilled water and suspended with 1.4 g 4-phenyl-trans-cyclohexane-1,2-diamine-dihydrogensulphate. Then the pH value is set to 7 with 0.5 N NaOH and maintained at this value with 0.1 N NaOH, wherein the pH value is continuously measured with a pH meter. The precipitate formed is drawn off gradually over a POR 4 glass filter crucible and dried in the desiccator over phosphorus pentoxide.

Appearance:
  yellow solid

Yield:
  1.2 g=2.63 mmol=55%

EXAMPLE 1

(SP-4-3)-(4-methyl-trans-cyclohexane-1,2-diamine)oxalatoplatinum (II)

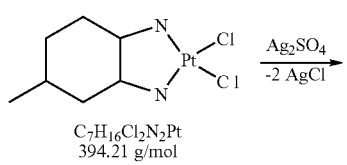

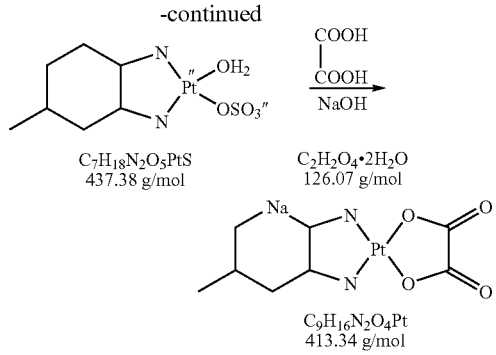

Preparation:
  0.8036 g=2.039 mmol (4-methyl-trans-dach)PtCl₂ 0.623 g=2.00 mmol Ag₂SO₄ 0.193 g=1.531 mmol oxalic acid dihydrate 3 ml 0.5 M NaOH 0.8036 g (4-methyl-trans-dach)PtCl₂ are well suspended in 30 ml tridistilled water. Then 0.6433 g Ag₂SO₄ are permanently added and the preparation stirred for 2 days with protection against light.

The precipitated AgCl is filtered off and the filtrate evaporated down to dryness on the rotary evaporator. From the residue 70 mg are taken for the elementary analysis and NMR spectroscopy. 0.193 g oxalic acid dihydrate and 3 ml 0.5 M NaOH are added to 669 mg=1.53 mmol aqua(4-methyl-trans-cyclohexane-1,2-diamine)sulphatoplatinum (II) and stirred overnight. The white solid is filtered off over a G4 glass filter crucible and dried in the vacuum desiccator over phosphorus pentoxide.

Aqua(4-methyl-trans-cyclohexane-1,2-diamine)sulphatoplatinum (II)

Appearance:
  yellow solid

Yield:
  0.739 g=1.690 mmol=85%

| Elementary analysis: calculated for C₇H₁₈N₂O₅PtS 0.2.H₂SO₄ 437.38 g/mol | | | | | | |
|---|---|---|---|---|---|---|
| | C | H | N | O | Pt | S |
| calculated: | 18.40 | 4.06 | 6.13 | 20.31 | 42.69 | 8.52 |
| found: | 18.54 | 3.99 | 5.94 | | | |
| found: | 18.57 | 4.03 | 5.95 | | | |

(SP-4-3)-(4-methyl-trans-cyclohexane-1,2-diamine)oxalatoplatinum (II)

Appearance:
  white solid

Melting point:
  >270° C. decomposition

Yield:
  0.310 g=0.75 mmol=50%

| Elementary analysis: calculated for $C_9H_{16}N_2O_4Pt$ 411.33 g/mol | | | | | |
|---|---|---|---|---|---|
| | C | H | N | O | Pt |
| calculated: | 26.28 | 3.92 | 6.81 | 15.48 | 47.20 |
| found: | 26.33 | 3.67 | 6.62 | | |
| found: | 26.30 | 3.70 | 6.60 | | |

IR spectrum [370–7000 cm$^{-1}$, CsI], characteristic bands (in cm$^{-1}$):

| 3243 | ν(N—H) |
|---|---|
| 2948, 2873 | ν(C—H) |
| 1668 | ν$_{as}$(C=O) |
| 1663 | δ(N—H) |

NMR spectra:

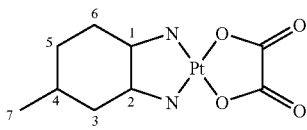

$^1$H-NMR spectrum in H$_2$O/D$_2$O 9/1: δ=0.75–0.87 [m, 1H, H(5)], 0.83 [d, 3H, H(7), $^3J_{H,H}$=6.60 Hz], 0.88–0.99 [m, 1H, H(3)], 1.19–1.40 [m, 2H, H(4), H(6)], 1.41–1.51 [m, 1H, H(5)], 1.86–1.97 [m, 2H, H(6) and H(3)], 2.18–2.41 [m, 2H, H(1) and H(2)], 3.50–3.60 [mm, 2H, H(1') and H(2')], 5.03 NH$_2$, 5.73 NH$_2$. $^{13}$C-NMR spectrum in H$_2$O/D$_2$O 9/1:

δ=17.1 [C(7')], 20.4 [C(7)], 26.9 [C(6')], 27.4 [C(4')], 29.7 [C(5')], 31.0 [C(6)], 31.3 [C(4)], 32.6 [C(5)], 39.8 [C(3')], 39.9 [C(3)], 62.4–62.4 [4C, C(1), C(2), C(1') and C(2')], 168.7 [2C, C=O]. $^{15}$N signal from the $^{15}$N, $^1$H-COSY spectrum in H$_2$O/D$_2$O 9/1: δ=−34.58/5.73 [NH$_2$]

EXAMPLE 2

(SP-4-3)-(4-ethyl-trans-cyclohexane-1,2-diamine) oxalatoplatinum (II)

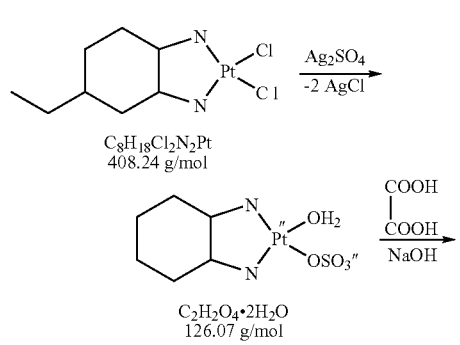

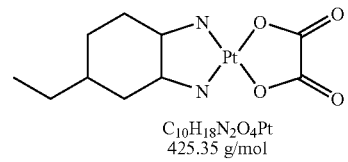

$C_{10}H_{18}N_2O_4Pt$
425.35 g/mol

Preparation:
0.8052 g=1.972 mmol (4-ethyl-trans-dach)PtCl$_2$ 0.584 g=1.87 mmol Ag$_2$SO$_4$ 48 g=1.972 mmol oxalic acid dihydrate 4 ml 0.5 M NaOH 0.8052 g (4-ethyl-trans-dach)PtCl$_2$ are well suspended in 30 ml tridistilled water. Then 0.584 g Ag$_2$SO$_4$ are permanently added and the preparation stirred for 5 days with protection against light. The precipitated AgCl is filtered off and the filtrate evaporated down to dryness on the rotary evaporator. 0.248 g oxalic acid dihydrate and 4 ml 0.5 M NaOH are added to the residue and stirred overnight. The white solid is filtered off over a G4 glass filter crucible and dried in the vacuum desiccator over phosphorus pentoxide.

Appearance:
white solid

Melting point:
>290° C. decomposition

Yield:
0.170 g=1.48 mmol=72%

| Elementary analysis: calculated for $C_{10}H_{18}N_2O_4Pt$ 425.35 g/mol | | | | | |
|---|---|---|---|---|---|
| | C | H | N | O | Pt |
| calculated: | 28.24 | 4.27 | 6.59 | 15.05 | 45.87 |
| found: | 28.00 | 4.02 | 6.75 | | |

IR spectrum [370–7000 cm$^{-1}$, CsI], characteristic bands (in cm$^{-1}$):

| 3100 | ν(N—H) |
|---|---|
| 2960, 2934, 2861 | ν(C—H) |
| 1706 | ν$_{as}$(C=O) |
| 1665 | δ(N—H) |

NMR spectra:

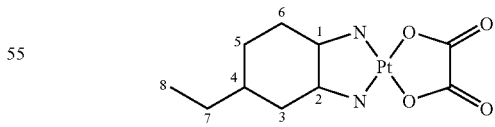

$^1$H-NMR spectrum in H$_2$O/D$_2$O 9/1: δ=0.69–0.85 [m, 1H, H(5)], 0.75 [t, 3H, H(8), $^3J_{H,H}$=7.09 Hz], 0.86–0.99 [m, 1H, H(3)], 1.07–1.31 [m, 4H, H(4), H(6), H(7)], 1.49–1.60 [m, 1H, H(S)], 1.89-2.03 [m, 2H, H(6) and H(3)], 2.21–2.41 [m, 2H, H(1) and H(2)], 5.75 NH$_2$.

$^{13}$C signals from the $^{13}$C, $^1$H COSY NMR spectrum in H$_2$O/D$_2$O 9/1: δ=11.1 [C(8)], 27.9 [C(7)], 30.1 [C(5)], 30.8 [C(6)], 37.5 [C(3)], 37.9 [C(4)], 62.5 [2C, C(1), C(2)].

EXAMPLE 3

(SP-4-3)-(4,5-dimethyl-trans-cyclohexane-1,2-diamine)oxalatoplatinum (II)

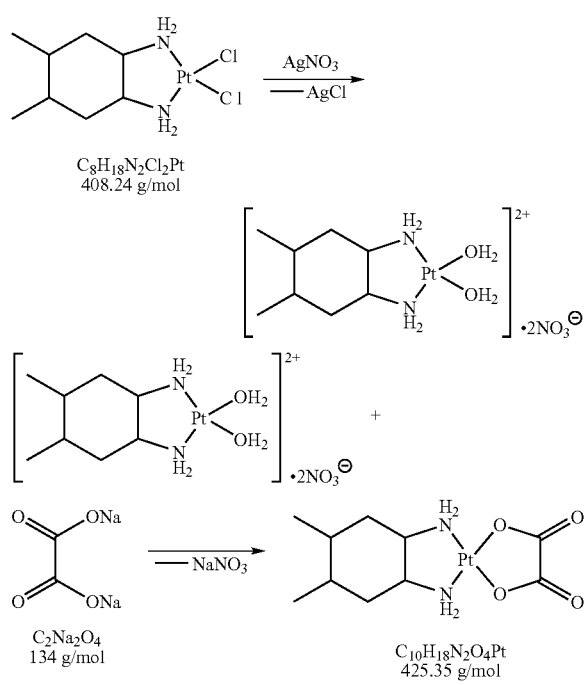

Preparation:

600 mg=1.47 mmol dichloro(4,5-dimethyl-cyclohexane-1,2-diamine)platinum (II) 480 mg=2.82 mmol $AgNO_3$ 127 mg=1.41 mmol oxalic acid 2.80 ml=2.80 mmol 1 N NaOH 600 mg dichloro(4,5-dimethyl-cyclohexane-1,2-diamine) platinum (II) are suspended in 70 ml of tridistilled water, 480 mg silver nitrate are added and stirred for one day at room temperature. The precipitated silver chloride is filtered off over a POR 4-glass filter crucible.

127 mg oxalic acid are dissolved in 2.8 ml NaOH and added to the above solution, which is reduced down to half. The mixture is stirred for 4 hours at room temperature. The ensuing product is drawn off over a POR 4-glass filter crucible and dried over phosphor pentoxide in a vacuum.

Appearance:

white solid

Yield:

290 mg=0.68 mmol=48%

| Elementary analysis: calculated for $C_{10}H_{18}N_2O_4Pt$ 425.35 g/mol | | | | | |
|---|---|---|---|---|---|
|  | C | H | N | O | Pt |
| calculated: | 28.24 | 4.27 | 6.59 | 15.05 | 45.87 |
| found: | 28.11 | 4.02 | 6.41 |  |  |

NMR spectrum:

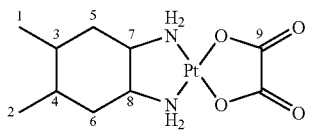

$^1$H-NMR in $D_2O$: δ=0.71–0.73 [d, 3H, H(1)], 0.8–0.82 [d, 3H, H(2)], 1.43–1.49 [m, 1H, H(3) and H(4)], 1.65–1.70 [m, 2H, H(5) or H(6)], 1.79–1.84 [m, 2H, H(5) or H(6)], 2.28–2.36 [m, 1H, H(7) or H(8)], 2.45–2.52 [m, 1H, H(8) or H(9)].

$^{13}$C-NMR in $D_2O$: δ=11.44 [(C1)], 17.94 [C(2)], 32.61 [(C3)], 33.85 [C(4)], 33.89 [(C5)], 38.25 [(C6)], 58.15 [C(7) and C(8)], 62.81 [C(7) and C(8)], 168.71 [C(9)].

EXAMPLE 4

(SP-4-3)-(4-propyl-trans-cyclohexane-1,2-diamine)oxalatoplatinum (II)

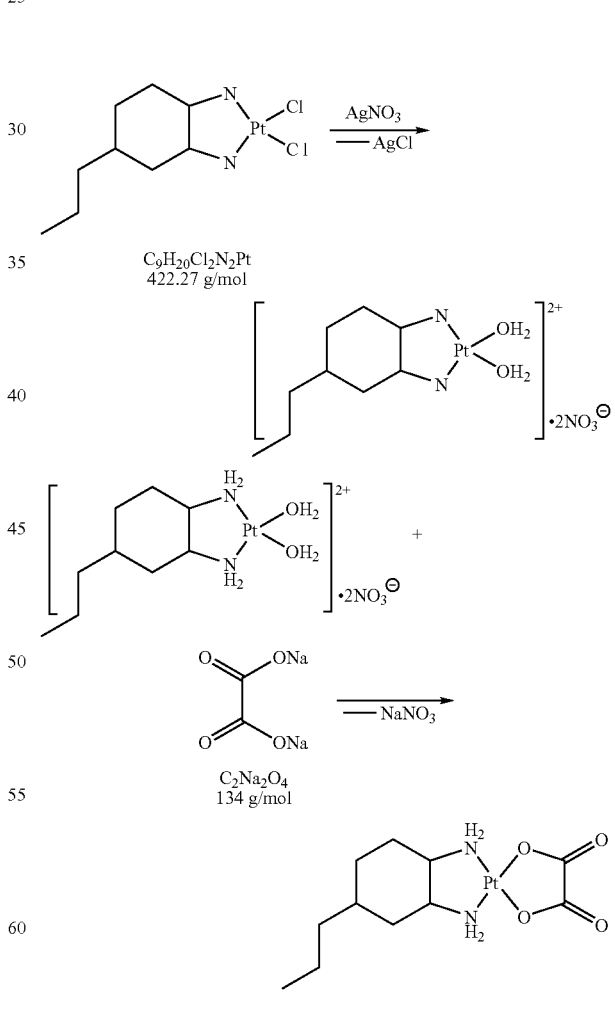

The synthesis occurs analogously to Example 3 from the dichloro complex.

Elementary analysis: calculated for C$_{11}$H$_{20}$N$_2$O$_4$Pt 439.38 g/mol

|  | C | H | N |
|---|---|---|---|
| calculated: | 30.07 | 4.59 | 6.37 |
| found: | 29.78 | 4.67 | 6.45 |

EXAMPLE 5

(SP-4-3)-(4-t-butyl-trans-cyclohexane-1,2-diamine) oxalatoplatinum (II)

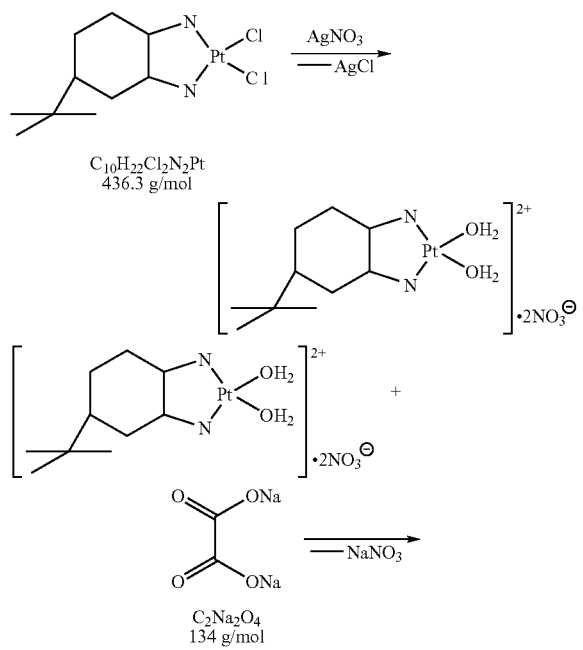

The synthesis occurs analogously to Example 3 from the dichloro complex.

Elementary analysis: calculated for C$_{12}$H$_{22}$N$_2$O$_4$Pt 453.41 g/mol

|  | C | H | N |
|---|---|---|---|
| calculated: | 31.79 | 4.89 | 6.18 |
| found: | 31.61 | 4.72 | 6.12 |

EXAMPLE 6

(SP-4-3)-(4-phenyl-trans-cyclohexane-1,2-diamine) oxalatoplatinum (II)

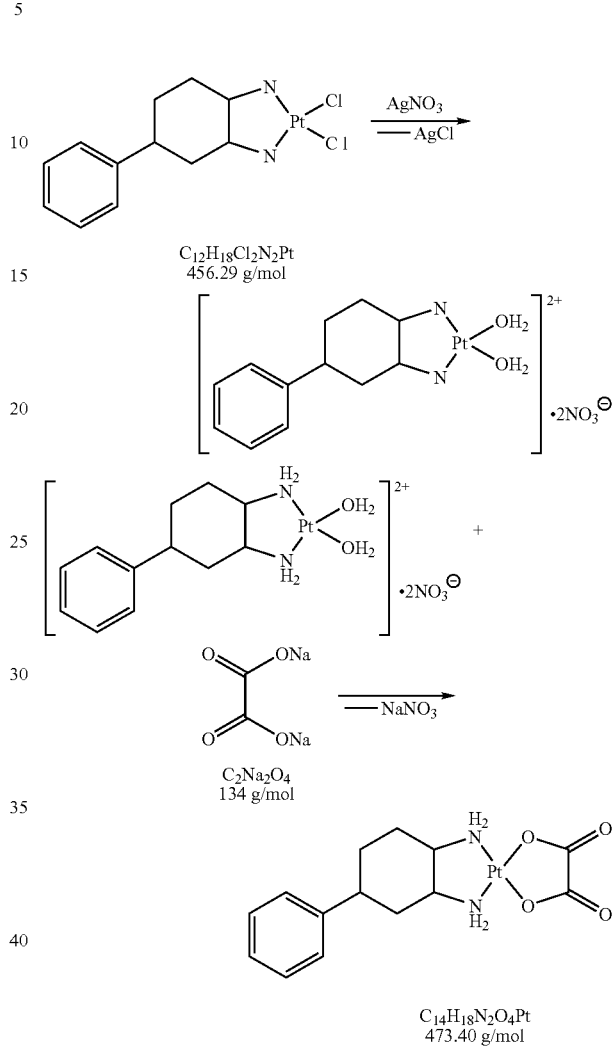

The synthesis occurs analogously to Example 3 from the dichloro complex.

Elementary analysis: calculated for C$_{14}$H$_{18}$N$_2$O$_4$Pt 473.40 g/mol

|  | C | H | N |
|---|---|---|---|
| calculated: | 35.52 | 3.83 | 5.92 |
| found: | 35.28 | 3.71 | 5.82 |

Carrying Out the Racemic Compound Splitting

The separation of the enantiomers of the diamines in the synthesis examples 3, 6, 15, 18, 21 and 24 can, for example, be carried out by forming the salts with tartaric acid. To do this, either (R,R)- or (S,S)-tartaric acid (depending on which enantiomer of the diamine is to be preferentially isolated) is dissolved in water and the diamine is added at a temperature of <70° C. After the complete addition of the diamine, glacial acetic acid is added and then the mixture is cooled to 5° C. The precipitated salt is filtered off and dried. By the addition of sodium hydroxide solution and the ensuing extraction with an organic solvent, it can be released and obtained.

Alternatively, O,O-dibenzoyl tartaric acid can be used instead of tartaric acid and then work proceeds in a water/acetone mixture.

The diamines obtained, clear of enantiomers, are then converted to the dichloroplatinum complexes analogously to the synthesis examples 7, 8, 25, 26, 27 and 28 and they can, after activation with silver nitrate or silver sulphate, be converted to the oxalato complexes with oxalic acid or sodium oxalate analogously to the examples 1–6.

Cytotoxicity Tests

The cytotoxicity of the compounds according to Examples 1 and 2 was tested by using the following cell lines 41M, CH1 and SW480. In this respect the following method was selected:

The proliferation-inhibiting activity of oxaliplatinum and its derivatives [(trans-S,S-chxn)Pt(ox)], [(4-methyl-trans-chxn)Pt(ox)] and [(4-ethyl-trans-chxn)Pt(ox)] was comparatively examined on 3 human tumor cell lines in the Microculture Tetrazolium Test (MTT assay) with continuous active substance exposition (96 h). In this regard, adherent monolayer cultures of the following cell lines were used: 41M (adenocarcinoma of the ovary), CH1 (adenocarcinoma of the ovary), SW480 (adenocarcinoma of the colon; primary resistance to cisplatinum).

Culture conditions: The cells were kept in 75 cm$^2$ culture flasks at 37° C. and moist atmosphere (5% $CO_2$). Minimal Essential Medium (MEM) was used as culture medium, with 2 mmol/l I-glutamine, 1 mmol/l sodium pyruvate, 50 IU/ml penicillin, 50 μg/ml streptomycin and 10% heat-inactivated foetal bovine serum.

Test execution: Cell suspensions were obtained from subconfluent cultures by treatment with trypsin and seeded in defined density in 96-well microculture plates. The initial density was selected such that for the complete test duration an exponential growth of the cultures was guaranteed. For the cell line 41M this was 4·10$^4$ cells/ml, for CH1 1.25·10$^4$ cells/ml and for SW480 1.5·10$^4$ cells/ml. The plates were incubated for 24 h under standard conditions to achieve cell establishment. Then the compounds to be tested were introduced in ten-staged concentration series in the culture medium (without addition of organic solvents or dissolving agents) into the plates and left for the complete test duration (96 h). Per experiment each concentration was tested on eight microcultures of the same cell line. At the end of the experiment the respective number of living cells in the microculture was determined spectrophotometrically (at 550 nm) using the MTT-dye reaction in relationship to the untreated control cultures. Equally, the number of living cells in microculture plates started in parallel was quantified at the start of the active substance exposition. The testing of [(trans-S,S-chxn)Pt(ox)] and the racemic compound was carried out once, all other experiments were carried out three times. The mean values were used for the evaluation.

Results with the Cell Line 41M

| Compound | $IC_{50}$ | $GL_{50}$ | TGI | $LC_{50}$ |
|---|---|---|---|---|
| Oxaliplatinum | 4.3 ± 1.4 | 0.67 ± 0.04 | 5.5 ± 2.8 | 17.7 ± 0.7 |
| [(trans-S,S-chxn)Pt(ox)] | 3.2 | 1.11 | 4.4 | 19.8 |
| [(trans-chxn)Pt(ox)] | 4.2 | 0.99 | 5.0 | 33.1 |
| [(4-methyl-trans-chxn)Pt(ox)] | 2.4 ± 0.5 | 0.91 ± 0.16 | 4.2 ± 2.6 | 17.9 ± 7.0 |
| [(4-ethyl-trans-chxn)Pt(ox)] | 2.4 ± 1.4 | 0.70 ± 0.32 | 3.0 ± 0.4 | 15.1 ± 5.1 |

FIG. 1 shows a graphical representation of the results in dependence of the concentration [μM] and the living cells (T/C) [%].

Results with the Cell Line CH1

| Substance | IC50 | Gl50 | TGI | LC50 |
|---|---|---|---|---|
| Oxaliplatinum | 0.27 ± 0.22 | 0.42 ± 0.21 | 1.8 ± 0.4 | 3.6 ± 0.7 |
| [(trans-S,S-chxn)Pt(ox)] | 1.5 | 1.14 | 4.2 | 8.4 |
| [(trans-chxn)Pt(ox)] | 0.7 | 0.54 | 2.0 | 4.0 |
| [(4-methyl-trans-chxn)Pt(ox)] | 0.34 ± 0.10 | 0.22 ± 0.03 | 0.93 ± 0.22 | 1.9 ± 0.4 |
| [(4-ethyl-trans-chxn)Pt(ox)] | 0.30 ± 0.20 | 0.21 ± 0.14 | 0.98 ± 0.59 | 2.1 ± 1.1 |

Figure 2:
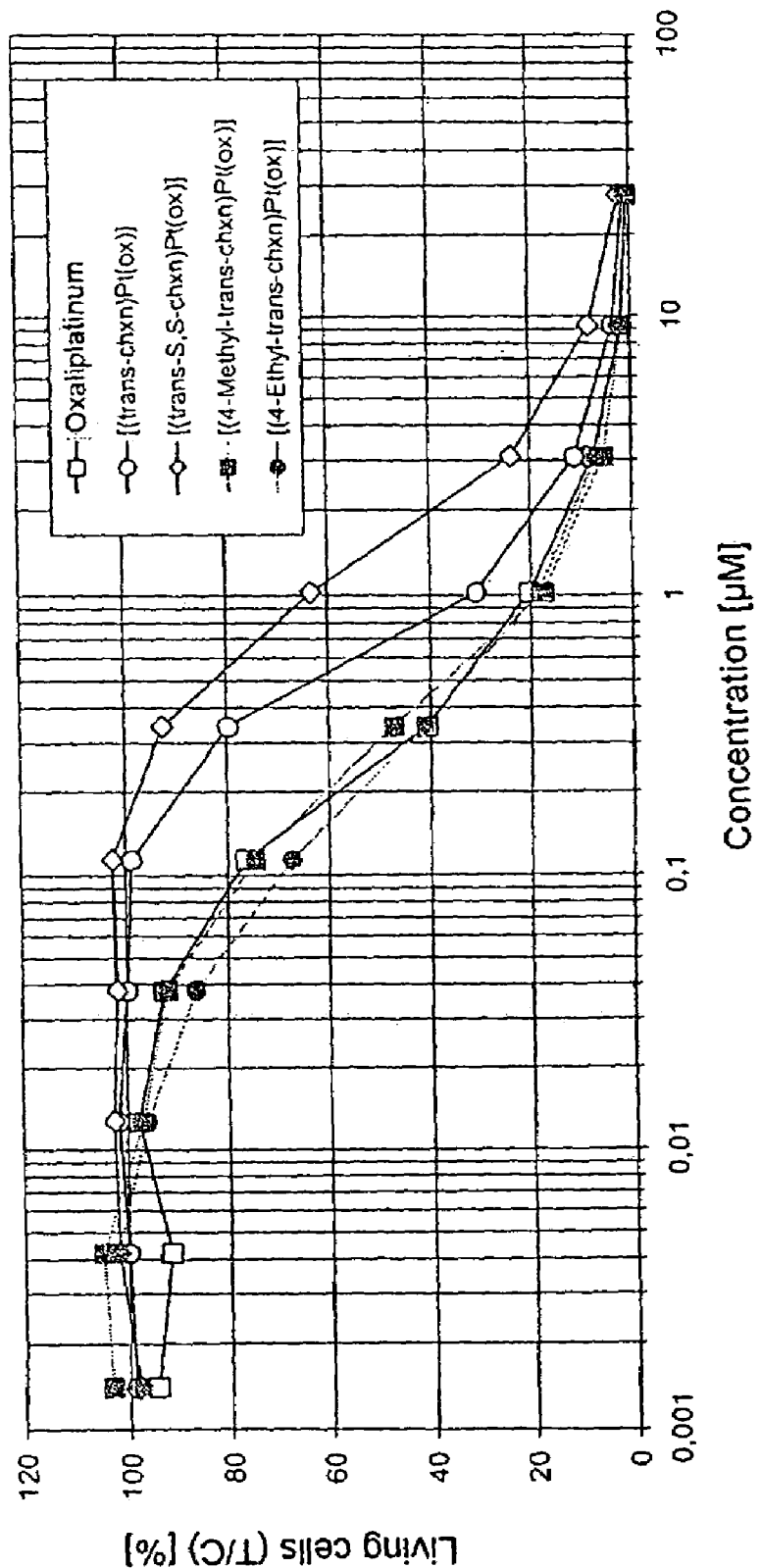
FIG. 2 is a graphical representation of the cytotoxicity test results of the compounds of Examples 1 and 2 plotting the CH1 cell line of living cells (T/C) [%] against concentration [μM]

FIG. 2 shows a graphical representation of the results in dependence of the concentration [μM] and the living cells (T/C) [%].

Results with the Cell Line SW480

| Substance | IC50 | Gl50 | TGI | LC50 |
|---|---|---|---|---|
| Oxaliplatinum | 0.67 ± 0.28 | 0.17 ± 0.07 | 16.2 ± 2.7 | 230 ± 23 |
| [(trans-S,S-chxn)Pt(ox)] | 4.2 | 2.2 | 47.8 | 70.4 |
| [(trans-chxn)Pt(ox)] | 1.6 | 0.8 | 21.8 | 104.6 |
| [(4-methyl-trans-chxn)Pt(ox)] | 0.65 ± 0.07 | 0.31 ± 0.11 | 9.0 ± 2.9 | 73.3 ± 48.9 |
| [(4-ethyl-trans-chxn)Pt(ox)] | 0.61 ± 0.42 | 0.30 ± 0.23 | 9.1 ± 5.3 | 21.0 ± 5.0 |

Figure 3:
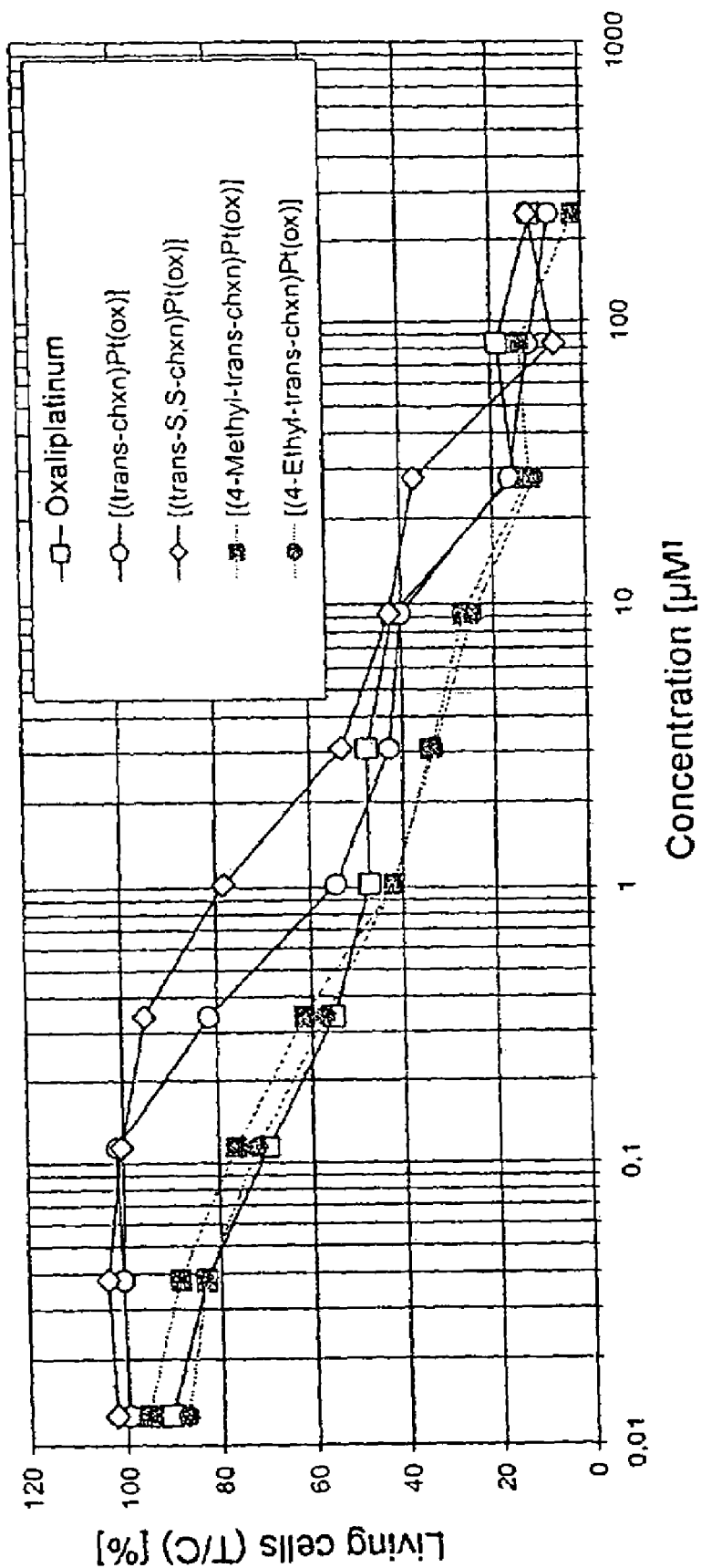
FIG. 3 is a graphical representation of the cytotoxicity test results of the compounds of Examples 1 and 2 plotting the SW480 cell line of living cells (T/C) [%] against concentration [μM]

FIG. 3 shows a graphical representation of the results in dependence of the concentration [μM] and the living cells (T/C) [%].

As can be seen from the above results, in comparison to oxaliplatinum, the cytotoxicity of the isomer mixtures of the compounds according to Examples 1 and 2 is comparable or better. This is particularly surprising, because isomer mixtures generally have a lower cytotoxicity than pure trans-R,R-cyclohexane-1,2-diamine-platinum compounds.

In Vivo Experiments

Conducted efficacy studies show a clearly lower toxicity of the new derivatives compared to oxaliplatinum itself. The use of oxaliplatinum in the highest dosage leads to the death of all animals in the test group up to day 14, whereas in the groups, which have been administered the compounds according to the invention (4-methyl-trans-chxn)Pt(ox) and (4-ethyl-trans-chxn)Pt(ox) also in the highest dosage level, 4/6 animals ((4-methyl-trans-chxn)Pt(ox)) resp. 6/6 animals ((4-ethyl-trans-chxn)Pt(ox)) were still alive on day 14.

Schedule: Qd×5

Female, tumor-bearing B6D2F1 mouse, day 14 after tumor transplantation.

| Substance | Dose mg/kg | Survivors/total number |
|---|---|---|
| (4-methyl-trans-chxn)Pt(ox) | 1.30 | 6/6 |
| | 2.60 | 5/6 |
| | 5.20 | 4/6 |
| (4-ethyl-trans-chxn)Pt(ox) | 1.34 | 5/6 |
| | 2.68 | 6/6 |
| | 5.35 | 6/6 |
| Oxaliplatinum | 1.25 | 5/6 |
| | 2.50 | 6/6 |
| | 5.00 | 0/6 |

The effectiveness of the compounds according to the invention in the i.m. transplanted murine Lewis lung carcinoma was, despite the significantly better compatibility, comparable with the effect of oxaliplatinum.

L1210 Leukaemia in the Mouse

In this experiment the new compound (4-methyl-trans-chxn)Pt(ox) showed in mouse leukaemia both a better tolerance at high dosage (24 mg/kg) and also a better effectiveness in the region of 3 mg/kg and 6 mg/kg (all animals survived the experiment to the end), whereas in the group treated with l-OHP deaths already occurred.

Figure 4:
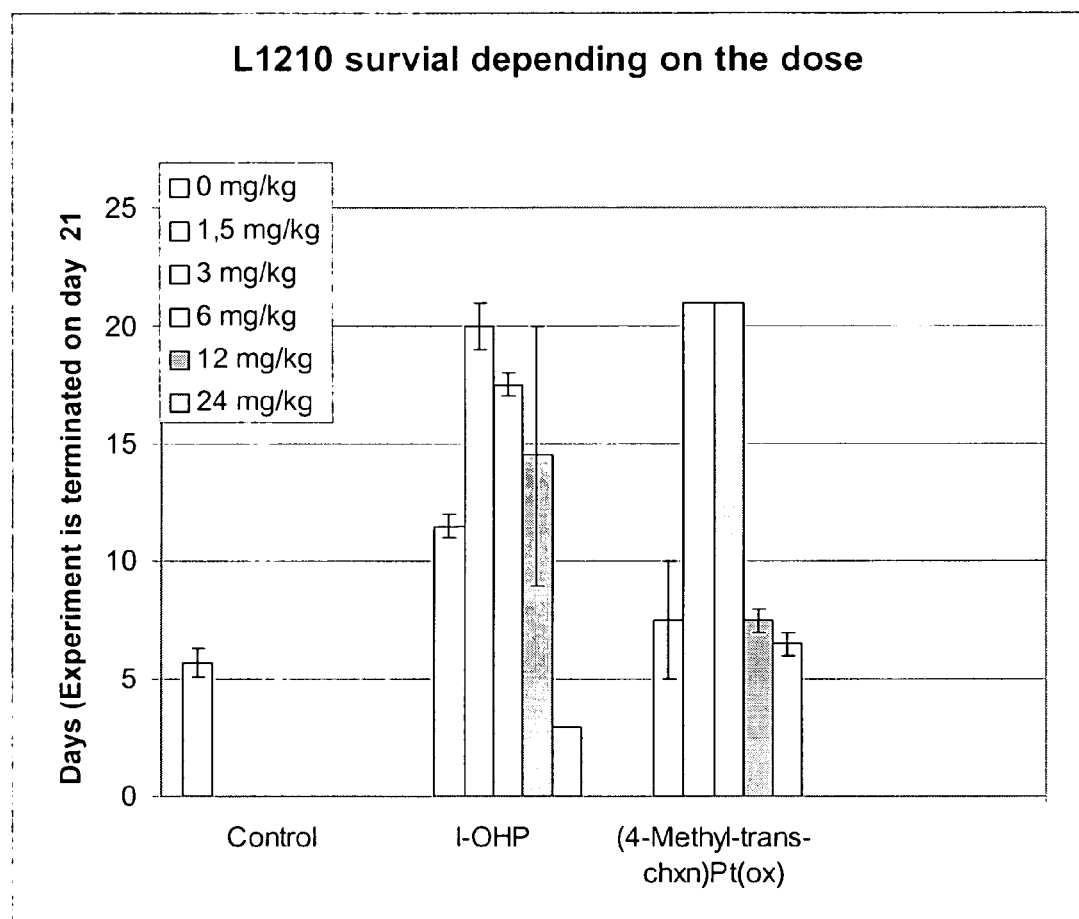
FIG. 4 is a bar graph of the results of the effectiveness of (4-methyl-trans-chxn)Pt(ox) in comparison to l-OHP in leukaemia L1210 in the mouse, plotting days of life against dosage.

FIG. 4 is a bar graph of the results of the effectiveness of (4-methyl-trans-chxn)Pt(ox) in comparison to l-OHP in leukaemia L1210 in the mouse at various dosages over a 21 day study.

Mtd Study

In this study on animals free of tumors the two new derivatives (4-methyl-trans-chxn)Pt(ox) and (4-ethyl-trans-chxn)Pt(ox) show a clearly better tolerance than can be found for oxaliplatinum (MTD in both cases 10 mg/kg Qd×5, weight loss 5% on day 5, in comparison: oxaliplatinum MTD=5 mg/kg with the same schedule).

Consequently, a better tolerance of the new derivatives according to the invention is found compared to the established oxaliplatinum in animal tests.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A compound of the general formula (I),

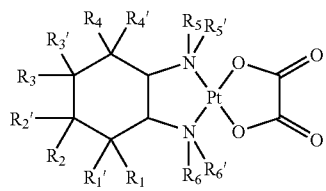

wherein the substituents $R^1$, $R^{1'}$, $R^2$, $R^{2'}$, $R^3$, $R^{3'}$, $R^4$, and $R^{4'}$ are independently selected from the group consisting of hydrogen, unsubstituted or substituted branched or unbranched alkyl, unsubstituted or substituted branched or unbranched alkenyl, unsubstituted or substituted cycloalkyl, unsubstituted or substituted cycloalkenyl, unsubstituted or substituted aryl and unsubstituted or substituted alkylaryl radicals, the substituents $R^5$, $R^{5'}$, $R^6$, and $R^{6'}$ are independently selected from the group consisting of hydrogen, unsubstituted or substituted branched or unbranched alkyl, and unsubstituted or substituted branched or unbranched alkenyl radicals, and wherein optionally in each case at least two of the substituents $R^1$, $R^{1'}$, $R^2$, $R^{2'}$, $R^3$, $R^{3'}$, $R^4$, and $R^{4'}$ can form with one another at least one unsubstituted or substituted alkylene, unsubstituted or substituted alkenylene radical or an unsubstituted or substituted aromatic ring, and wherein optionally at least one of the carbon atoms of the cyclohexane ring bearing the substituents $R^1$, $R^{1'}$, $R^2$, $R^{2'}$, $R^3$, $R^{3'}$, $R^4$, and $R^{4'}$ is replaced by a heteroatom, and if the heteroatom is oxygen, the substituents $R^1$, $R^{1'}$, $R^2$, $R^{2'}$, $R^3$, $R^{3'}$, $R^4$, and/or $R^{4'}$ can additionally be hydroxy radicals, and pharmaceutically compatible salts thereof, provided that at least one of the substituents $R^1$, $R^{1'}$, $R^2$, $R^{2'}$, $R^3$, $R^{3'}$, $R^4$, or $R^{4'}$ is not equal to hydrogen and the radicals $R^1$ or $R^{1'}$ and $R^4$ or $R^{4'}$ do not form any unsubstituted $C_{1-2}$-alkylene radicals with one another.

2. The compound according to claim 1, wherein the substituents $R^1$, $R^{1'}$, $R^2$, $R^{2'}$, $R^3$, $R^{3'}$, $R^4$, and $R^{4'}$ are selected independently from the group consisting of hydrogen, $C_1$–$C_{15}$-alkyl, $C_2$–$C_{15}$-alkenyl, $C_3$–$C_{15}$-cycloalkyl, $C_3$–$C_{15}$-cycloalkenyl, $C_6$–$C_{14}$-aryl and $C_1$–$C_{15}$-alkyl-$C_6$–$C_{14}$-aryl radicals.

3. The compound according to claim 1, wherein the substituents $R^1$, $R^{1'}$, $R^2$, $R^{2'}$, $R^3$, $R^{3'}$, $R^4$, and $R^{4'}$ are selected from the group consisting of hydrogen, $C_1$–$C_{10}$-alkyl, $C_3$–$C_{10}$-cycloalkyl, $C_6$–$C_{14}$-aryl radicals.

4. The compound according to claim 1, wherein the substituents $R^1$, $R^{1'}$, $R^3$, $R^{3'}$, $R^4$, and $R^{4'}$ are equal to hydrogen and one of the substituents $R^2$ or $R^{2'}$ is a $C_1$–$C_6$-alkyl radical or $C_6$–$C_{14}$-aryl radical and the other is a hydrogen atom.

5. The compound according to claim 4, wherein the substituents $R^2$ or $R^{2'}$ are methyl, ethyl, propyl, t-butyl or phenyl radicals.

6. The compound according to claim 1, wherein the substituents $R^5$, $R^{5'}$, $R^6$, and $R^{6'}$ are hydrogen and optionally at least one of the carbon atoms of the cyclohexane ring bearing the substituents $R^1$, $R^{1'}$, $R^2$, $R^{2'}$, $R^3$, $R^{3'}$, $R^4$, and $R^{4'}$ is replaced by a heteroatom, and if the heteroatom is oxygen, the substituents $R^1$, $R^{1'}$, $R^2$, $R^{2'}$, $R^3$, $R^{3'}$, $R^4$, and $R^{4'}$ are selected independently from the group consisting of hydrogen, unsubstituted or substituted alkyl, unsubstituted or substituted alkenyl, unsubstituted or substituted cycloalkyl, unsubstituted or substituted cycloalkenyl, unsubstituted or substituted aryl and unsubstituted or substituted alkylaryl radicals.

7. The compound according to claim 1 as a therapeutic agent for treatment of cancer and cancerous tumors.

8. A medicament comprising a compound according to claim 1, for treatment of cancer and cancerous tumors in a mammal.

9. A method of therapeutic treatment of a mammal requiring treatment, comprising administering an effective amount of a compound according to claim 1 for treatment of cancer and cancerous tumors.

* * * * *